(12) United States Patent
Hemmati-Brivanlou et al.

(10) Patent No.: US 6,197,947 B1
(45) Date of Patent: Mar. 6, 2001

(54) TRANSLATION INITIATION FACTOR 4AIII AND METHODS OF USE THEREOF

(75) Inventors: Ali Hemmati-Brivanlou; Daniel C. Weinstein, both of New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/318,443

(22) Filed: May 25, 1999

Related U.S. Application Data

(60) Provisional application No. 60/087,575, filed on Jun. 1, 1998.

(51) Int. Cl.[7] .................................................. C07H 21/04
(52) U.S. Cl. ...................... 536/23.5; 536/23.4; 435/70.1; 435/71.2; 435/325
(58) Field of Search ................................ 536/23.1, 23.5; 435/70.1, 325, 467, 472, 476, 477

(56) References Cited

U.S. PATENT DOCUMENTS

| | | |
|---|---|---|
| 4,816,397 | 3/1989 | Boss et al. . |
| 4,816,567 | 3/1989 | Cabilly et al. . |
| 5,399,346 | 3/1995 | Anderson et al. . |
| 5,625,048 | 4/1997 | Tsien et al. . |

OTHER PUBLICATIONS

Belsham et al., Microbial. Rev., 60:499–511 (1996).
Benoist and Chambon, Nature, 290:304–310 (1981).
DeBoer et al., Proc. Natl. Acad. Sci. U.S.A., 80:21–25 (1983).
Edge, Nature, 292:756 (1981).
Fodor et al. Science 251:767–773 (1991).
Geysen et al., Molecular Immunology 23:709–715 (1986).
Graff et al., Cell, 79:169 (1994).
Grunz and Tacke, Cell Diff. Devl., 28:211 (1989).
Hemmati–Brivanlou et al., Cell 77:273–281 (1994).
Hemmati–Brivanlou et al., Development, 111:715 (1991).
Jonas et al., Proc. Natl. Acad. Sci. USA, 82:5143 (1985).
Jonas et al., Development 111:531–42 (1991).
Kaplitt et al., Molec. Cell. Neurosci. 2:320–330 (1991).
Klein and Melton, Science, 265:803 (1994).
Lamb et al. (1993) Science 262:713–718.
Lasko and Ashburner, Nature, 335:611 (1988).
Mohun et al., Nature, 311:716 (1984).
Rhoads, Curr. Opin. Cell Biol., 3:1019 (1991).
Rozen et al., Mol. Cell. Biol., 10:1134 (1990).
Sasai et al., Cell 79:779–790 (1994).
Scott and Smith, 1990, Science 249:386–390 (1990).
Sonenberg, in Translational Control, J.W.B. Hershey, M.B. Matthews, and N. Sonenberg, Eds., Cold Spring Harbor Press, New York, pp. 245–269 (1996).
Suzuki, Proc. Natl. Acad. Sci. USA 91:10255–59 (1994).
Villa–Kamaroff et al., Proc. Natl. Acad. Sci. U.S.A., 75:3727–3731 (1978).
Wagner et al., Proc. Natl. Acad. Sci. U.S.A., 78:1441–1445(1981).
Wilson and Hemmati–Brivanlou, Nature, 376:331 (1995).
Xu et al., Biochem. Biophys. Res. Commun., 212:212 (1995).
Yamamoto et al., Cell, 22:787–797 (1980).

*Primary Examiner*—Donna C. Wortman
*Assistant Examiner*—Robert Zeman
(74) *Attorney, Agent, or Firm*—Darby & Darby

(57) ABSTRACT

The present invention provides a vertebrate translation initiation factor (eIF-4AIII), that plays a role in the differentiation of an embryonic cell to an epideimal cell. This translation initiation factor interacts with BMP-4 in a positive regulatory loop. The nucleic acid and amino acid sequences are also disclosed. Also disclosed are methods of using the translation initiation factor, nucleic acids encoding the same, and corresponding antibodies and the like.

11 Claims, 6 Drawing Sheets

FIG. IE

|  | MeIF-4AI | MeIF-4AII | NeIF-4A3 |
|---|---|---|---|
| XeIF-4AIII | 64 | 66 | 73 |
| MeIF-4AI |  | 90 | 62 |
| MeIF-4AII |  |  | 62 |

FIG. IA

```
1    M A A A A V A G V A G L T T A H A K R L L R E E D M T T V E    XeIF-4AIII
1    M E E D R L V                                                  NeIF-4A3

31   F Q T S E E V D V T P T F D T M G L R E D L L R G I Y A Y G    XeIF-4AIII
8    F E T S K G V E P I A S F A E M G I K D D L L R G V Y Q Y G    NeIF-4A3

61   F E K P S A I Q Q K A I K Q I   K G R D V I A Q S Q S G T G    XeIF-4AIII
38   F E K P S A I Q Q R A V L P I I S G R D V I A Q A Q S G T G    NeIF-4A3

91   K T A T F C V S V L Q C L D I Q I R E T Q A L I L A P T K E    XeIF-4AIII
68   K T S M I A L T V C Q I V D T K S S E V Q A L I L S P T R E    NeIF-4A3

121  L A R Q I Q K V L L A L G D Y M N V Q C H A C I G G T N V G    XeIF-4AIII
98   L A A Q T E K V I L A I G D Y I N V Q A H A C I G G K S V G    NeIF-4A3

151  E D I R K L D Y G Q H V V A G T P G R V F D M I R R R S L R    XeIF-4AIII
128  E D I R K L E H G V Q V V S G T P G R V C D M I K R R T L R    NeIF-4A3
```

FIG. 1B

```
181  T R A I K M L V L D E A D E M L N K G F K E Q I Y D V Y R Y   XeIF-4AIII
158  T R G I K L L I L D E S D E M L S R G F K D Q I Y D V Y R Y   NeIF-4A3

211  L P P A T Q V C L I S A T L P H E I L E M T N K F M T D P I   XeIF-4AIII
188  L P P E L Q V V L I S A T L P N E I L E I T S K F M T D P V   NeIF-4A3

241  R I L V K R D E L T L E G I K Q F F V A V E R E E W K F D T   XeIF-4AIII
218  R I L V K R D E L T L E G I K Q F F V A V E K E E W K F D T   NeIF-4A3

271  L C D L Y D T L T I T Q A V I F C N T K R K V D W L T E K M   XeIF-4AIII
248  L C D L Y D T L T I T Q A V I F C N T K R K V D W L T S K M   NeIF-4A3

301  R E A N F T V S S M H G D M P Q K E R E S I M K E F R S G A   XeIF-4AIII
278  R E N N F T V S S M H G D M P Q K E R D A I M A E F R G G T   NeIF-4A3

331  S R V L I S T D V W A R G L D V P Q V S L I N Y D L P N N   XeIF-4AIII
308  T R V L I T T D V W A R G L D V Q Q V S L V I N Y D L P N N   NeIF-4A3

361  R E L Y I H R I G R S G R Y G R K G V A I N F V K N D D I R   XeIF-4AIII
338  R E L Y I H R I G R S G R F G R K G V A I N F V K S D D I K   NeIF-4A3

391  I L R D I E Q Y Y S T Q I D E M P M N V A D L I             XeIF-4AIII
368  I L R D I E Q Y Y S T Q I D E M P M N V A D L I             NeIF-4A3
```

FIG. 1C
FIG. 1D
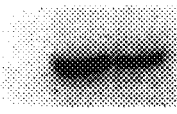

dissociation/no reaggregation dissociation/ reaggregation

SEQUENCE LISTING

<160> NUMBER OF SEQ ID NOS: 12

<210> SEQ ID NO 1
<211> LENGTH: 1245
<212> TYPE: DNA
<213> ORGANISM: Xenopus laevis

<400> SEQUENCE: 1

```
atggcggccg cagctgttgc aggagttgcc gggttgacca cggcgcacgc gaagcggctt      60
ttacgggagg aggatatgac caccgtggag ttccagacca gcgaagaagt ggatgtaacg     120
ccaacgtttg atacgatggg gctgagggaa gaccttctga gaggcatcta tgcttatgga     180
tttgagaaac catcggctat acaacagaag gcaatcaagc agatcatcaa aggaagggat     240
gtgatcgcac aatcacagtc tggtacaggc aaaacagcaa cttttttgtgt ttctgtgcta     300 cagtgtttgg atattcagat ccgtgaaacc caagccttga ttttagcacc caccaaagag     360
ttagcacggc aaaattcagaa ggtgttgctt gctttgggg actacatgaa tgtgcagtgt     420
```

-continued

```
catgcgtgta ttggaggcac aaatgttgga gaggatatcc gaaaattgga ttatgggcag    480
cacgttgttg ctggaacacc agggcgtgtt tttgatatga ttcgacgcag aagtttaaga    540
actcgggcca ttaaaatgtt agtgctggat gaagctgatg aaatgttgaa taagggtttc    600
aaggagcaaa tttatgatgt atacaggtat ctgcctccag caacacaagt ttgtttaatc    660
agtgctaccc tgccacatga aatcctggaa atgaccaata agtttatgac tgatcccatc    720
cgtatccttg tgaaacgtga tgagttgaca ctggaaggca tcaagcagtt ttttgtggca    780
gtggagagag aagagtggaa atttgatact ttgtgtgatt tatatgacac tttgactatt    840
acacaagctg taatcttctg caacaccaaa agaaaggtag attggttgac tgaaaaaatg    900
agagaagcaa atttcacagt ttcgtcaatg catggtgata tgccccaaaa ggagagagag    960
tcaatcatga aagaattccg atctggtgca agccgagtcc tcatatcaac ggacgtctgg   1020
gcccgaggat tggatgtgcc acaggtctcc ttgattatca actatgatct tcccaataac   1080
cgagaattgt acattcacag aattggccga tcaggaagat atggaagaaa gggtgttgcc   1140
attaactttg tcaagaatga tgacatccgt attttaagag atattgagca gtactattcg   1200
acccagattg atgaaatgcc aatgaacgtt gctgatctta tttga                   1245
```

<210> SEQ ID NO 2
<211> LENGTH: 415
<212> TYPE: PRT
<213> ORGANISM: Xenopus laevis

<400> SEQUENCE: 2

```
Met Ala Ala Ala Val Ala Gly Val Ala Gly Leu Thr Thr Ala His
  1               5                  10                  15

Ala Lys Arg Leu Leu Arg Glu Glu Asp Met Thr Thr Val Glu Phe Gln
             20                  25                  30

Thr Ser Glu Glu Val Asp Val Thr Pro Thr Phe Asp Thr Met Gly Leu
         35                  40                  45

Arg Glu Asp Leu Leu Arg Gly Ile Tyr Ala Tyr Gly Phe Glu Lys Pro
     50                  55                  60

Ser Ala Ile Gln Gln Lys Ala Ile Lys Gln Ile Ile Lys Gly Arg Asp
 65                  70                  75                  80

Val Ile Ala Gln Ser Gln Ser Gly Thr Gly Lys Thr Ala Thr Phe Cys
                 85                  90                  95

Val Ser Val Leu Gln Cys Leu Asp Ile Gln Ile Arg Glu Thr Gln Ala
            100                 105                 110

Leu Ile Leu Ala Pro Thr Lys Glu Leu Ala Arg Gln Ile Gln Lys Val
        115                 120                 125

Leu Leu Ala Leu Gly Asp Tyr Met Asn Val Gln Cys His Ala Cys Ile
    130                 135                 140

Gly Gly Thr Asn Val Gly Glu Asp Ile Arg Lys Leu Asp Tyr Gly Gln
145                 150                 155                 160

His Val Val Ala Gly Thr Pro Gly Arg Val Phe Asp Met Ile Arg Arg
                165                 170                 175

Arg Ser Leu Arg Thr Arg Ala Ile Lys Met Leu Val Leu Asp Glu Ala
            180                 185                 190

Asp Glu Met Leu Asn Lys Gly Phe Lys Glu Gln Ile Tyr Asp Val Tyr
        195                 200                 205

Arg Tyr Leu Pro Pro Ala Thr Gln Val Cys Leu Ile Ser Ala Thr Leu
    210                 215                 220
```

Pro His Glu Ile Leu Glu Met Thr Asn Lys Phe Met Thr Asp Pro Ile
225                 230                 235                 240

Arg Ile Leu Val Lys Arg Asp Glu Leu Thr Leu Glu Gly Ile Lys Gln
                245                 250                 255

Phe Phe Val Ala Val Glu Arg Glu Trp Lys Phe Asp Thr Leu Cys
                260                 265                 270

Asp Leu Tyr Asp Thr Leu Thr Ile Thr Gln Ala Val Ile Phe Cys Asn
            275                 280                 285

Thr Lys Arg Lys Val Asp Trp Leu Thr Glu Lys Met Arg Glu Ala Asn
290                 295                 300

Phe Thr Val Ser Ser Met His Gly Asp Met Pro Gln Lys Glu Arg Glu
305                 310                 315                 320

Ser Ile Met Lys Glu Phe Arg Ser Gly Ala Ser Arg Val Leu Ile Ser
                325                 330                 335

Thr Asp Val Trp Ala Arg Gly Leu Asp Val Pro Gln Val Ser Leu Ile
                340                 345                 350

Ile Asn Tyr Asp Leu Pro Asn Asn Arg Glu Leu Tyr Ile His Arg Ile
                355                 360                 365

Gly Arg Ser Gly Arg Tyr Gly Arg Lys Gly Val Ala Ile Asn Phe Val
370                 375                 380

Lys Asn Asp Asp Ile Arg Ile Leu Arg Asp Ile Glu Gln Tyr Tyr Ser
385                 390                 395                 400

Thr Gln Ile Asp Glu Met Pro Met Asn Val Ala Asp Leu Ile Glx
                405                 410                 415

<210> SEQ ID NO 3
<211> LENGTH: 532
<212> TYPE: DNA
<213> ORGANISM: Homo sapiens

<400> SEQUENCE: 3

```
aagcagatca tcaaagggag agatgtcatc gcacagtctc agtccggcac aggaaaaaca    60
gccaccttca gtatctcagt cctccagtgt ttggatattc aggttcgtga aactcaagct   120
ttgatcttgg ctcccacaag agagttggct gtgcagatcc agaaggggct gcttgctctc   180
ggtgactaca tgaatgtcca gtgccatgcc tgcattggag caccaatgt tggcgaggac    240
atcaggaagc tggattacgg acagcatgtt gttgcgggca ctccagggcg tgtttttgat   300
atgattcgtc gcagaagcct aaggacacgt gctatcaaaa tgttggtttt ggatgaagct   360
gatgaaatgt tgaataaagg tttcaaagag cagatttacg atgtatacag gtacctgcct   420
ccagccacac aggtggttct catcagtgcc acgctgccac acgagattct ggagatgacc   480
aacaagttca tgaccgaccc aatccgcatc ttggtgggaa ttcctgcagc cc           532
```

<210> SEQ ID NO 4
<211> LENGTH: 177
<212> TYPE: PRT
<213> ORGANISM: Homo sapiens

<400> SEQUENCE: 4

Lys Gln Ile Ile Lys Gly Arg Asp Val Ile Ala Gln Ser Gln Ser Gly
1               5                   10                  15

Thr Gly Lys Thr Ala Thr Phe Ser Ile Ser Val Leu Gln Cys Leu Asp
                20                  25                  30

Ile Gln Val Arg Glu Thr Gln Ala Leu Ile Leu Ala Pro Thr Arg Glu
            35                  40                  45

| Leu | Ala | Val | Gln | Ile | Gln | Lys | Gly | Leu | Leu | Ala | Leu | Gly | Asp | Tyr | Met |
| | 50 | | | | | 55 | | | | | 60 | | | | |
| Asn | Val | Gln | Cys | His | Ala | Cys | Ile | Gly | Gly | Thr | Asn | Val | Gly | Glu | Asp |
| 65 | | | | | 70 | | | | | 75 | | | | | 80 |
| Ile | Arg | Lys | Leu | Asp | Tyr | Gly | Gln | His | Val | Val | Ala | Gly | Thr | Pro | Gly |
| | | | | 85 | | | | | 90 | | | | | 95 | |
| Arg | Val | Phe | Asp | Met | Ile | Arg | Arg | Ser | Leu | Arg | Thr | Arg | Ala | Ile |
| | | | 100 | | | | | 105 | | | | | 110 | |
| Lys | Met | Leu | Val | Leu | Asp | Glu | Ala | Asp | Glu | Met | Leu | Asn | Lys | Gly | Phe |
| | | 115 | | | | | 120 | | | | | 125 | | | |
| Lys | Glu | Gln | Ile | Tyr | Asp | Val | Tyr | Arg | Tyr | Leu | Pro | Pro | Ala | Thr | Gln |
| | 130 | | | | | 135 | | | | | 140 | | | | |
| Val | Val | Leu | Ile | Ser | Ala | Thr | Leu | Pro | His | Glu | Ile | Leu | Glu | Met | Thr |
| 145 | | | | | 150 | | | | | 155 | | | | | 160 |
| Asn | Lys | Phe | Met | Thr | Asp | Pro | Ile | Arg | Ile | Leu | Val | Gly | Ile | Pro | Ala |
| | | | | 165 | | | | | 170 | | | | | 175 | |
| Ala |

<210> SEQ ID NO 5
<211> LENGTH: 1536
<212> TYPE: DNA
<213> ORGANISM: Homo sapiens

<400> SEQUENCE: 5

```
cggcagcgag gtcggcagcg gcacagcgag gtcggcagcg gcgcgcgctg tgctcttccg      60
cggactctga atcatggcga ccacggccac gatggcgacc tcgggctcgg cgcgaaagcg     120
gctgctcaaa gaggaagaca tgactaaagt ggaattcgag accagcgagg aggtggatgt     180
gacccccacg ttcgacacca tgggcctgcg ggaggacctg ctgcggggca tctacgctta     240
cggttttgaa aaaccatcag caatccagca acgagcaatc aagcagatca tcaaagggag     300
agatgtcatc gcacagtctc agtccggcac aggaaaaaca gccaccttca gtatctcagt     360
cctccagtgt ttggatattc aggttcgtga aactcaagct tgatcttgg ctcccacaag     420
agagttggct gtgcagatcc agaaggggct gcttgctctc ggtgactaca tgaatgtcca     480
gtgccatgcc tgcattggag gcaccaatgt tggcgaggac atcaggaagc tggattacgg     540
acagcatgtt gtcgcgggca ctccagggcg tgttttttgat atgattcgtc gcagaagcct     600
aaggacacgt gctatcaaaa tgttggtttt ggatgaagct gatgaaatgt tgaataaagg     660
tttcaaagag cagatttacg atgtatacag gtacctgcct tcagccacac aggtggttct     720
catcagtgcc acgctgccac acgagattct ggagatgacc aacaagttca tgaccgaccc     780
aatccgcatc ttggtgaaac gtgatgaatt gactctggaa ggcatcaagc aattttttcgt     840
ggcagtggag agggaagagt ggaaatttga cactctgtgt gacctctacg acacactgac     900
catcactcag gcggtcatct tctgcaacac caaaagaaag gtggactggc tgacggagaa     960
aatgaggga gccaacttca ctgtatcctc aatgcatgga gacatgcccc agaaagagcg    1020
ggagtccatc atgaaggagt tccggtcggg cgccagccga gtgcttattt ctacagatgt    1080
ctgggccagg gggttggatg tccctcaggt gtccctcatc attaactatg atctccctaa    1140
taacagagaa ttgtacatac acagaattgg gagatcaggt caatacggcc ggaagggtgt    1200
ggccattaac tttgtaaaga atgacgacat ccgcatcctc agatatcg agcagtacta    1260
ttccactcag attgatgaga tgccgatgaa cgttgctgat cttatctgaa gcagcagatc    1320
agtgggatga gggagactgt tcacctgctg tgtactcctg tttggaagta tttagatcca    1380
```

```
gattctactt aatggggttt atatggactt tcttctcata aatggcctgc cgtctccctt   1440
cctttgaaga ggatatgggg attctgctct cttttcttat ttacatgtaa ataatacatt   1500
gttctaagtc tttttcatta aaaatttaaa acttta                             1536
```

<210> SEQ ID NO 6
<211> LENGTH: 411
<212> TYPE: PRT
<213> ORGANISM: Homo sapiens

<400> SEQUENCE: 6

```
Met Ala Thr Thr Ala Thr Met Ala Thr Ser Gly Ser Ala Arg Lys Arg
 1               5                  10                  15

Leu Leu Lys Glu Glu Asp Met Thr Lys Val Phe Glu Thr Ser Glu
             20                  25                  30

Glu Val Asp Val Thr Pro Thr Phe Asp Thr Met Gly Leu Arg Glu Asp
         35                  40                  45

Leu Leu Arg Gly Ile Tyr Ala Tyr Gly Phe Glu Lys Pro Ser Ala Ile
     50                  55                  60

Gln Gln Arg Ala Ile Lys Gln Ile Ile Lys Gly Arg Asp Val Ile Ala
 65                  70                  75                  80

Gln Ser Gln Ser Gly Thr Gly Lys Thr Ala Thr Phe Ser Ile Ser Val
                 85                  90                  95

Leu Gln Cys Leu Asp Ile Gln Val Arg Glu Thr Gln Ala Leu Ile Leu
            100                 105                 110

Ala Pro Thr Arg Glu Leu Ala Val Gln Ile Gln Lys Gly Leu Leu Ala
        115                 120                 125

Leu Gly Asp Tyr Met Asn Val Gln Cys His Ala Cys Ile Gly Gly Thr
    130                 135                 140

Asn Val Gly Glu Asp Ile Arg Lys Leu Asp Tyr Gly Gln His Val Val
145                 150                 155                 160

Ala Gly Thr Pro Gly Arg Val Phe Asp Met Ile Arg Arg Arg Ser Leu
                165                 170                 175

Arg Thr Arg Ala Ile Lys Met Leu Val Leu Asp Glu Ala Asp Glu Met
            180                 185                 190

Leu Asn Lys Gly Phe Lys Glu Gln Ile Tyr Asp Val Tyr Arg Tyr Leu
        195                 200                 205

Pro Ser Ala Thr Gln Val Val Leu Ile Ser Ala Thr Leu Pro His Glu
    210                 215                 220

Ile Leu Glu Met Thr Asn Lys Phe Met Thr Asp Pro Ile Arg Ile Leu
225                 230                 235                 240

Val Lys Arg Asp Glu Leu Thr Leu Glu Gly Ile Lys Gln Phe Phe Val
                245                 250                 255

Ala Val Glu Arg Glu Glu Trp Lys Phe Asp Thr Leu Cys Asp Leu Tyr
            260                 265                 270

Asp Thr Leu Thr Ile Thr Gln Ala Val Ile Phe Cys Asn Thr Lys Arg
        275                 280                 285

Lys Val Asp Trp Leu Thr Glu Lys Met Arg Glu Ala Asn Phe Thr Val
    290                 295                 300

Ser Ser Met His Gly Asp Met Pro Gln Lys Glu Arg Glu Ser Ile Met
305                 310                 315                 320

Lys Glu Phe Arg Ser Gly Ala Ser Arg Val Leu Ile Ser Thr Asp Val
                325                 330                 335

Trp Ala Arg Gly Leu Asp Val Pro Gln Val Ser Leu Ile Ile Asn Tyr
```

|   | 340 |   |   |   | 345 |   |   |   | 350 |   |   |
|---|---|---|---|---|---|---|---|---|---|---|---|
| Asp | Leu | Pro | Asn | Asn | Arg | Glu | Leu | Tyr | Ile | His | Arg | Ile | Gly | Arg | Ser |
|   |   |   | 355 |   |   |   | 360 |   |   |   | 365 |

Gly Gln Tyr Gly Arg Lys Gly Val Ala Ile Asn Phe Val Lys Asn Asp
         370                 375                 380

Asp Ile Arg Ile Leu Arg Asp Ile Glu Gln Tyr Tyr Ser Thr Gln Ile
385                 390                 395                 400

Asp Glu Met Pro Met Asn Val Ala Asp Leu Ile
                405                 410

<210> SEQ ID NO 7
<211> LENGTH: 1682
<212> TYPE: DNA
<213> ORGANISM: Homo sapiens

<400> SEQUENCE: 7

```
cagcggcaca gcgaggtcgg cagcggcaca gcgaggtcgg cagcggcaca gcgaggtcgg        60
cagcggcaca gcgaggtcgg cagcggcaca gcgaggtcgg cagcggcaca gcgaggtcgg       120
cagcggcagc gaggtcggca gcggcacagc gaggtcggca gcggcagcga ggtcggcagc       180
ggcgcgcgct gtgctcttcc gcggactctg aatcatggcg accacggcca cgatggcgac       240
ctcgggctcg gcgcgaaagc ggctgctcaa agaggaagac atgactaaag tggaattcga       300
gaccagcgag gaggtggatg tgacccccac gttcgacacc atgggcctgc gggaggacct       360
gctgcgggc atctacgctt acggttttga aaaaccatca gcaatccagc aacgagcaat        420
caagcagatc atcaaaggga gagatgtcat cgcacagtct cagtccggca caggaaaaac       480
agccaccttc agtatctcag tcctccagtg tttggatatt caggttcgtg aaactcaagc       540
tttgatcttg gctcccacaa gagagttggc tgtgcagatc cagaaggggc tgcttgctct       600
cggtgactac atgaatgtcc agtgccatgc ctgcattgga ggcaccaatg ttggcgagga       660
catcaggaag ctggattacg acagcatgt tgtcgcgggc actccagggc gtgttttga        720
tatgattcgt cgcagaagcc taaggacacg tgctatcaaa atgttggttt tggatgaagc       780
tgatgaaatg ttgaataaag gtttcaaaga gcagatttac gatgtataca ggtacctgcc       840
tccagccaca caggtggttc tcatcagtgc cacgctgcca cacagagatc tggagatgac       900
caacaagttc atgaccgacc caatccgcat cttggtgaaa cgtgatgaat tgactctgga       960
aggcatcaag caattttttcg tggcagtgga gagggaagag tggaaatttg acactctgtg      1020
tgacctctac gacacactga ccatcactca ggcggtcatc ttctgcaaca ccaaaagaaa      1080
ggtggactgg ctgacggaga aaatgaggga agccaacttc actgtatcct caatgcatgg      1140
agacatgccc cagaaagagc gggagtccat catgaaggag ttccgtcgg gcgccagccg       1200
agtgcttatt tctacagatg tctgggccag ggggttggat gtccctcagg tgtccctcat      1260
cattaactat gatctcccta ataacagaga attgtacata cacagaattg ggagatcagg      1320
tcgatacggc cggaagggtg tggccattaa ctttgtaaag aatgacgaca tccgcatcct      1380
cagagatatc gagcagtact attccactca gattgatgag atgccgatga acgttgctga      1440
tcttatctga agcagcagat cagtgggatg agggagactg ttcacctgct gtgtactcct      1500
gtttggaagt atttagatcc agattctact taatggggtt tatatggact ttcttctcat      1560
aaatggcctg ccgtctccct tcctttgaag aggatatggg gattctgctc tcttttctta      1620
tttacatgta aataatacat tgttctaagt cttttttcatt aaaaatttaa aacttttccc      1680
at                                                                     1682
```

<210> SEQ ID NO 8
<211> LENGTH: 411
<212> TYPE: PRT
<213> ORGANISM: Homo sapiens

<400> SEQUENCE: 8

```
Met Ala Thr Thr Ala Thr Met Ala Thr Ser Gly Ser Ala Arg Lys Arg
  1               5                  10                  15

Leu Leu Lys Glu Glu Asp Met Thr Lys Val Glu Phe Glu Thr Ser Glu
             20                  25                  30

Glu Val Asp Val Thr Pro Thr Phe Asp Thr Met Gly Leu Arg Glu Asp
         35                  40                  45

Leu Leu Arg Gly Ile Tyr Ala Tyr Gly Phe Glu Lys Pro Ser Ala Ile
     50                  55                  60

Gln Gln Arg Ala Ile Lys Gln Ile Ile Lys Gly Arg Asp Val Ile Ala
 65                  70                  75                  80

Gln Ser Gln Ser Gly Thr Gly Lys Thr Ala Thr Phe Ser Ile Ser Val
                 85                  90                  95

Leu Gln Cys Leu Asp Ile Gln Val Arg Glu Thr Gln Ala Leu Ile Leu
            100                 105                 110

Ala Pro Thr Arg Glu Leu Ala Val Gln Ile Gln Lys Gly Leu Leu Ala
        115                 120                 125

Leu Gly Asp Tyr Met Asn Val Gln Cys His Ala Cys Ile Gly Gly Thr
    130                 135                 140

Asn Val Gly Glu Asp Ile Arg Lys Leu Asp Tyr Gly Gln His Val Val
145                 150                 155                 160

Ala Gly Thr Pro Gly Arg Val Phe Asp Met Ile Arg Arg Ser Leu
                165                 170                 175

Arg Thr Arg Ala Ile Lys Met Leu Val Leu Asp Glu Ala Asp Glu Met
            180                 185                 190

Leu Asn Lys Gly Phe Lys Glu Gln Ile Tyr Asp Val Tyr Arg Tyr Leu
        195                 200                 205

Pro Pro Ala Thr Gln Val Val Leu Ile Ser Ala Thr Leu Pro His Glu
    210                 215                 220

Ile Leu Glu Met Thr Asn Lys Phe Met Thr Asp Pro Ile Arg Ile Leu
225                 230                 235                 240

Val Lys Arg Asp Glu Leu Thr Leu Glu Gly Ile Lys Gln Phe Phe Val
                245                 250                 255

Ala Val Glu Arg Glu Glu Trp Lys Phe Asp Thr Leu Cys Asp Leu Tyr
            260                 265                 270

Asp Thr Leu Thr Ile Thr Gln Ala Val Ile Phe Cys Asn Thr Lys Arg
        275                 280                 285

Lys Val Asp Trp Leu Thr Glu Lys Met Arg Glu Ala Asn Phe Thr Val
    290                 295                 300

Ser Ser Met His Gly Asp Met Pro Gln Lys Glu Arg Glu Ser Ile Met
305                 310                 315                 320

Lys Glu Phe Arg Ser Gly Ala Ser Arg Val Leu Ile Ser Thr Asp Val
                325                 330                 335

Trp Ala Arg Gly Leu Asp Val Pro Gln Val Ser Leu Ile Ile Asn Tyr
            340                 345                 350

Asp Leu Pro Asn Asn Arg Glu Leu Tyr Ile His Arg Ile Gly Arg Ser
        355                 360                 365

Gly Arg Tyr Gly Arg Lys Gly Val Ala Ile Asn Phe Val Lys Asn Asp
```

```
                370              375              380
Asp Ile Arg Ile Leu Arg Asp Ile Glu Gln Tyr Tyr Ser Thr Gln Ile
385                 390              395              400

Asp Glu Met Pro Met Asn Val Ala Asp Leu Ile
                    405              410

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 9
gggtgttgcc attaactttg tc                                              22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 10
cctgccacat gaaatcctgg                                                 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 11
gagtcgcagt ctggatattg c                                               21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 12
tggaatgtag ccagtctgcc                                                 20
```

TRANSLATION INITIATION FACTOR 4AIII AND METHODS OF USE THEREOF

CROSS-REFERENCE TO RELATED APPLICATIONS

The present application is a non-provisional application claiming the priority of copending provisional U.S. Ser. No. 60/087,575 filed Jun. 1, 1998, the disclosure of which is hereby incorporated by reference in its entirety. Applicants claim the benefits of this application under 35 U.S.C. §119(e).

GOVERNMENTAL SUPPORT

The research leading to the present invention was supported, at least in part, by a grant from NIH Grant No. HD 32105-01. Accordingly, the Government may have certain rights in the invention.

FIELD OF THE INVENTION

This invention relates generally to a vertebrate translation initiation factor 4AIII, to methods and compositions utilizing the factor, and to the antibodies reactive toward the factor, in assays and for diagnosing, preventing and/or treating cellular debilitation, derangement or dysfunction.

BACKGROUND OF THE INVENTION

The induction of the nervous systeim one of the earliest and most dramatic events of vertebrate development, has challenged and frustrated embryologists since the organizer graft experiments of Spemann and Mangold. Classical work established that the gastrula stage ectodeim of amphibian and other vertebrate embryos gives rise to the neural plate in response to signals from the adjacent dorsal mesodeii (Spemaim's orgarizer). In the absence of this influence, as on the ventral side or in explants made before gastrulation, the ectodeim differentiates only as epiderims. Thus, development as epidermiis was generally assumed to be a fallback, or default fate for the gastl-ula ectodeim requiring no cell-cell comunication, while neural specification was contingent on receipt of signals. However, much effort over several decades failed to identify the chemical substances responsible for neural induction in the embryo, though a variety of rather curious materials were found to be able to neutralize salamander ectoderm. Recent studies of the amphibian embryo have identified three diffusible factors with neural inducing ability: noggin (Lamb et al., 1993), follistatin (Hernati-Brivailou et al., 1994) and chordin (short gastrulation) (Sasai et al., 1995; Sasai et al., 1994). All three factors mimic the signal(s) which emanates from the organizer and converts ventral ectoderm (epidermis) to dorsal ectoderm (nervous tissue).

Other recent work has led to a second promising molecular candidate for a neural inducing signal and at the same time suggested a new twist on the long-held classical model of neural and epiderrnal specification. First, Gruz and others revealed that Xenopus ectoderm cultured during early gastrula stages as a dispersed cell population formed neural tissue even though it receives no signals from the mesodenn during this period. More recently, Brivanlou and Melton discovered that injection of a dominanit-negative fonn of the activin receptor could neuralize ectodennal explants, again in the apparent absence of mesodenm Finally, the activin antagonist follistatin could also cause neural differentiation. These fmdings led Brivaiilou and Melton to propose that the cells of the early gastrula animal cap are disposed to form neural tissue, in the absence of further influences. In this sense one could speak of a default neural fate for the ectoderm The neural "default model" of neural induction argues that the differentiation of epidermis requires inductive signals, while the neuralization of the dorsal ectoderm requires only an inhibition of this signaling.

Epidermal specification, and thus the inhibition of neural fate, results from cell-cell commuiication within the prospective ectoderm When this signaling is interrupted, by dispersing the cells or by molecular antagollists, neural tissue forms. Neural induction by the dorsal mesodeln, in this model, would work in the same way, that is by blocking epidermalizing signaling within the animal cap. Since both the truncated activin receptor and follistatin could accomplish this, activin seemed likely to be the factor that mediated epidermal specification. The further discovery that follistatin was expressed in the organizer region in Xenopus, firom where it could act to block activin signaling in the dorsal ectodeim and thus permit neural tissue to form, naturally suggested follistatin as an endogenous neural inducer. Although these were enticing speculations, there was no direct evidence that activin could act to specify epidermis.

More recently it has been disclosed that BMP-4, may be the endogenous neural inhibitor and epidermal inducer (see, U.S. patent application Ser. No. 08/413,047, filed Mar. 29, 1995, and U.S. patent application Ser. No. 08/622,860, filed Mar. 29, 1996 hereby incorporated herein in their entireties). Ectodermal ("animal cap") explants form epidermis when cultured intact; these explants will neuralize if subjected to prolonged dissociation [Grunz and Tacke, Cell Diff Devl., 28:211 (1989); Sato and Sargent, Dev. Biol., 134:263 (1989); Godsave and Slack, Dev. Biol., 134:486 (1989)]. Soluble BMP-4 can induce epidermis in dissociated ectoderm, substituting for the epidennal inducer presumably lost by dilution [Wilson and Hermati-Brivanlou, Nature, 376:331 (1995)].

BMP-4 is a member of a set of closely related proteins that form a subgroup witlihi the larger TGF-β superfamily of secreted growth factors that also includes activin and the TGF's proper. First purified firom bone as activities capable of promoting bone regrowth, the BMPs have more recently been found in early vertebrate embryos, where they appear to play a variety of roles. In Xenopus, several groups have shown that BMP-2 and BMP-4 are capable of inducing ventral mesoderm, as well as ventralizing mesoderm induced by activin. Recent work showing that BMP-4 is expressed in the ventral marginal zone, and that a dominant negative version of a BMP receptor has strong dorsalizing effects on early embryos lends further support to the idea that BMP-4 acts in vivo to ventralize the marginal zone. However, little is known with regard to factors that are involved in epidermal induction downstream in the BMP-4 signaling pathway. Therefore, there is a need to identify such factors in order to identify agents that can stimulate epidermal growth.

Protein translation rates increase in response to a variety of peptide growth factors [Rhoads, Curn. Opin. Cell Biol., 3:1019 (1991); Frederickson and Sonenberg, in Translational Regulation of Gene Expression, J. Illan, Ed., Plenum Press, New York, pp. 143–162 (1993)]. In several studies, soluble factors have been shown to enhance translation through the modification of cytoplasmic proteins involved in translation initiation [Sonenberg, in Translational Control, J. W. B. Hershey, M. B. Matthews, and N. Sonenberg, Eds., Cold Spring Harbor Press, New York, pp. 245–269 (1996)]. Interestingly, stimulation of the initiation machinery does not always result in a general increase in the rate of translation: various growth factor treatments can dramatically elevate the translation rates of specific mRNAs [Sonenberg, 1996, supra]. Enhanced activity of translation initiation factors may preferentially lead to the expression of mRNAs with a complex secondary structure in their 5' untranslated regions (UTR) [Sonenberg, 1996, supra; Brown and Schreiber, Cell, 86:517 (1996)]. This selective translation can have profound consequences for cell fate. For example, the overexpression of translation initiation factor eIF-4E in Xenopus embryos induces mesoderrn in cells that would otherwise develop as epidermis [Klein and Melton, Science, 265:803 (1994)]. Ectopic eIF-4E preferentially elevates the translation of mRNA encoding activin, a mesoderm-inducing growth factor.

eIF-4E, along with eIF-4A and eIF-4G, form the multi-subunit cap-binding complex eIF-4F. This initiation complex is thought to unwind secondary structure in the 5' UTR of mRNA to allow ribosome binding and thus initiate translation [Sonenberg, 1996, supra]. The helicase activity of eIF-4F is thought to be conferred by the eIF-4A subunit, in conjunction with eIF-4B [Rozen et al., Mol. Cell. Biol., 10:1134 (1990); Pause et al., EMBO J., 13:1205 (1994)]. Although other RNA helicases have been implicated in specific interactions with MRNA [Lasko and Ashbumer, Nature, 335:611 (1988); Hay et al., Cell, 55:577 (1988); Liang et al., Development, 120:1201 (1994)], no evidence has thus far demonstrated a role for the helicase component of the initiation complex in binding specificity.

There is presently a great need for generating neural and epideimal tissue for a variety of medical treatments. Manipulating cellular factors that are part of the pathways involved in the induction of either epideimal or neural cellular differentiation is a method likely to be successful for producing such tissues. Any of these factors along the pathway could conceivably be used in the induction of epideimal or neural cellular differentiation, or as targets for drug screens that are employed to identify molecules that will stimulate or inhibit the induction of epidermal or neural cellular differentiation.

The citation of any reference herein should not be construed as an adlmission that such reference is available as "Prior Art" to the instant application.

SUMMARY OF THE INVENTION

The present invention provides a novel animal translation initiation factor that plays a role in inducing epideimal foimation. More particularly, the present invention provides an anuimal eIF-4AIII that interacts with bone molphogenic proteiln-4 (BMP-4) through a positive feedback loop in the ventral ectoderm of the animal gastrula. In a preferred embodiment, the antimal translation initiation factor is a vertebrate translation initiation factor.

Therefore, the present invention provides an isolated nucleic acid encoding a vertebrate translation initiation factor 4AIII (eIF-4AIII) having an ainio acid sequence that is substantially homologous to that of SEQ ID NO:2. In a related embodiment the isolated nucleic acid encodes a vertebrate eIF-4AIII having the amino acid sequence of SEQ ID NO:2 with a conservative amino acid substitution. In another embodiment the isolated nucleic acid encodes an amino acid sequence having SEQ ID NO:2. One such embodiment is an isolated nucleic acid having the nucleotide sequence of SEQ ID NO:1.

Another embodiment of the present invention is an isolated nucleic acid that encodes a maimmalian eIF-4AIII protein which contains an amino acid sequence of SEQ ID NO:4 having a conservative amino acid substitution. In a related embodiment, the nucleic acid encodes a human protein that contains the amino acid sequence of SEQ ID NO:4. One such nucleic acid of this type contains the nucleic acid sequence of SEQ ID NO:3.

Yet another embodiment of the present invention is an isolated nucleic acid that encodes a mammalian eIF-4AIII protein which contains an amino acid sequence of SEQ ID NO:6 having a conservative amino acid substitution. In a related embodiment, the nucleic acid encodes a human protein that contains the amino acid sequence of SEQ ID NO:6. One such nucleic acid of this type contains the nucleic acid sequence of SEQ ID NO:5.

Still, another embodiment of the present invention is an isolated nucleic acid that encodes a mammalian eIF-4AIII protein which contains an amino acid sequence of SEQ ID NO:8 having a conservative amino acid substitution. In a related embodiment, the nucleic acid encodes a human protein that contains the amino acid sequence of SEQ ID NO:8. One such nucleic acid of this type contains the nucleic acid sequence of SEQ ID NO:7.

The present invention also includes nucleic acids containing 15 or more nucleotides, preferably 24 or more nucleotides, and more preferably 36 or more nucleotides which hybridize to a nucleotide sequence that encodes an eIF-4AIII of the present invention. In a more preferred embodiment, the nucleotide sequence is SEQ ID NO:1 or a fragment thereof, such as nucleotides 1 to 90 of the coding sequence of SEQ ID NO:1.

The present invention also provides oligonucleotide primers and probes capable of screening for the nucleic acids of the present invention. In a preferred embodiment of this type the primer or probe has specificity for a nucleic acid encoding an eIF-4AIII having the amino acid sequence of SEQ ID NO:2 or SEQ ID NO:2 having a conservative amino acid substitution. In a more preferred embodiment of the present invention, the primer or probe has specificity for a nucleic acid encoding a xenopus eIF-4AIII comprising the coding sequence of SEQ ID NO:1. In an embodiment of this type, the primer or probe has a nucleotide sequence of 15 to 48, (preferably 24 to 36 nucleotides) that is identical to a sequence contained in SEQ ID NO:1.

All of the isolated nucleic acids of the present invention can further comprise a heterologous nucleotide sequence. In one particular embodiment of this type an isolated nucleic acid contains the nucleotide sequence of SEQ ID NO:1, and further comprises a heterologous nucleotide sequence. In another particular embodiment of this type the nucleic acid encodes an eIF-4AIII having the amino acid sequence of SEQ ID NO:2 and further comprises a heterologous nucleotide sequence. In yet another particular embodiment, the nucleic acid encodes an eIF-4AIII having the amino acid sequence of SEQ ID NO:2 having a conservative ainhio acid substitution and further comprises a heterologous nucleotide sequence. In still aother embodiment the nucleic acid encodes an eIF-4AIII having the aino acid sequence of SEQ ID NO:2 but contains a nonconservative amino acid substitution which alters the functional properties of the eIF-4AIII and further comprises a heterologous nucleotide sequence.

In still another embodiment of this type a nucleic acid contains the nucleotide sequence of SEQ ID NO:3, and further comprises a heterologous nucleotide sequence. In another embodiment the nucleic acid encodes an eIF-4AIII having the amino acid sequence of SEQ ID NO:4 and further comprises a heterologous nucleotide sequence. In yet another embodiment, the nucleic acid encodes an eIF-4AIII having the amino acid sequence of SEQ ID NO:4 having a conservative aino acid substitution and further comprises a heterologous nucleotide sequence. In still another embodiment an isolated nucleic acid encodes a eIF-4AIII having the amino acid sequence of SEQ ID NO:4 but contains a nonconservative amino acid substitution which alters the functional properties of the eIF-4AIII and further comprises a heterologous nucleotide sequence.

In yet another embodiment of this type a nucleic acid contains the nucleotide sequence of SEQ ID NO:5 and further comprises a heterologous nucleotide sequence. In another embodiment the nucleic acid encodes an eIF-4AIII having the amino acid sequence of SEQ ID NO:6 and further comprises a heterologous nucleotide sequence. In stiff another embodiment, the nucleic acid encodes an eIF-4AIII having the amino acid sequence of SEQ ID NO:6 having a conservative amino acid substitution and further comprises a heterologous nucleotide sequence. In yet another embodiment the nucleic acid encodes a eIF-4AIII having the amino acid sequence of SEQ ID NO:6 but contains a nonconservative amino acid substitution which alters the functional properties of the eIF-4AIII and further comprises a heterologous nucleotide sequence.

In still another embodiment of this type a nucleic acid contains a nucleotide sequence of SEQ ID NO:7 and further comprises a heterologous nucleotide sequence. In another embodiment the nucleic acid encodes an eIF-4AIII having the amino acid sequence of SEQ ID NO:8 and further comprises a heterologous nucleotide sequence. In yet another embodiment, the nucleic acid encodes an eIF-4AIII having the amino acid sequence of SEQ ID NO:8 having a conservative amino acid substitution and further comprises a heterologous nucleotide sequence. In still another embodiment the nucleic acid encodes a eIF-4AIII having the amino acid sequence of SEQ ID NO:8 but contains a nonconservative amino acid substitution which alters the functional properties of the eIF-4AIII and further comprises a heterologous nucleotide sequence.

Another aspect of the present invention includes nucleic acids that encode or comprise fragments of the eIF-4AIIIs of the present invention. Any of these nucleic acids can further comprise a heterologous nucleotide sequence.

In addition, any of the isolated nucleic acids of the present invention can be operatively linked to an expression control sequence. The present invention further provides a mnicellular host transfoirmed or tranisfected with one of the nucleic acids of the present invention operatively linked to an expression control sequence. In addition, the present invention provides a method of expressing an eIF-4AIII, or fragment thereof, encoded by the nucleic acid comprising culturing the unicellular host in an appropriate cell culture medium wider conditions that provide for expression of the eIF-4AIII or fragment thereof, by the cell. In one particular embodiment of this type, the present invention provides a method that further comprises the step of purifying the eIF-4AIII or fragment thereof. The purified form of the eIF-4AIII, or fragment thereof, obtained by this method is also part of the present invention.

The present invention also provides recombinant viruses transformed with a nucleic acid of the present invention. In one particular embodiment of this type, the transformed recombinant virus is used in a gene therapy protocol for correcting an error or deficiency of eIF-4AIII. In an alternative embodiment, the transformed recombinant virus is used to further probe the role of eIF-4AIII in the cell.

The present invention fhrther provides an isolated and/or recombinant vertebrate translation initiation factor 4AIII (eIF-4AIII) having an amino acid sequence that is substantially homologous to that of SEQ ID NO:2. In a related embodiment the isolated vertebrate eIF-4AIII has the amino acid sequence of SEQ ID NO:2 with a conservative amino acid substitution. In a related embodiment the isolated eIF-4AIII has an amino acid sequence having SEQ ID NO:2.

Another embodiment of the present invention is an isolated mamiinalian eIF-4AIII protein which contains an amino acid sequence of SEQ ID NO:4 having a conservative amino acid substitution. In a related embodiment, the eIF-4AIII is a human protein that contains the amino acid sequence of SEQ ID NO:4.

Still another embodiment of the present invention is an isolated mammalian eIF-4AIII protein which contains an amino acid sequence of SEQ ID NO:6 having a conservative amino acid substitution. In a related embodiment, the eIF-4AIII is a human protein that contains the amino acid sequence of SEQ ID NO:6.

Yet, another embodiment of the present invention is an isolated mammalian eIF-4AIII protein which contains an amino acid sequence of SEQ ID NO:8 having a conservative amino acid substitution. In a related embodiment, the eIF-4AIII is a human protein that contains the amino acid sequence of SEQ ID NO:8.

The present invention also provides fusion proteins comprising an heterologous amino acid sequence and an eIF-4AIII or fragment thereof. In one such embodiment the eIF-4AIII has the amino acid sequence of SEQ ID NO:2. In another such embodiment the eIF-4AIII, comprises SEQ ID NO:2 with a conservative amino acid substitution. In still another such embodiment the eIF-4AIII or fragment thereof, comprises SEQ ID NO:4. In yet another such embodiment the eIF-4AIII or fragment thereof, comprises SEQ ID NO:4 with a conservative amino acid substitution. In still another such embodiment the eIF-4AIII or fragment thereof, comprises SEQ ID NO:6. In another such embodiment the eIF-4AIII or fragment thereof, comprises SEQ ID NO:6 with a conservative amino acid substitution. In still another such embodiment the eIF-4AIII or fragment thereof, comprises SEQ ID NO:8. In yet another such embodiment the eIF-4AIII or fragment thereof, comprises SEQ ID NO:8 with a conservative amino acid substitution. In one particular embodiment the heterologous amino acid sequence is the amino acid sequence of green fluorescent protein. In another such embodiment, the heterologous amino acid sequence is a FLAG peptide.

The present invention also provides antibodies to all of the eIF-4AIIIs and fragments of eIF-4AIII proteins, of the present invention. In a preferred embodiment the antibody is to a xenopus translation initiation factor 4AIII having the amino acid sequence of SEQ ID NO:2. In one such embodiment of this type, the antibody is a polyclonal antibody. In another embodiment the antibody is a monoclonal antibody. In a prefenred embodiment the monoclonal antibody is a chimeric antibody. The present invention also includes immortal cell lines that produce a monoclonal antibody of the present invention.

The present invention further provides methods of identifying potential drugs that modulate the ability of the eIF-4AIIIs of the present invention to induce the transcription of epidermal markers. One such embodiment comprises the step of administering an eIF-4AIII into an animal pole of an embryo in the presence of an agent (e.g., a potential drug). An animal pole explant is isolated from the embryo and subsequently cultured. The RNA of the animal pole is extracted and the transcription of an epideimal marker protein is assayed. The amount of transcription of the epidermal marker protein is then compared with that determined in a control procedure in which the agent was not included. An agent that enhances or diminishes the transcription of the epidelmal marker protein (relative to the control) is identified as a potential drug that modulates the ability of the eIF-4AIII to induce the transcription of epideimal markers.

In one particular embodiment the administering of the eIF-4AIII is performed by injecting an mRNA encoding the eIF-4AIII into the embryo. In a prefenred embodiment the embryo is a 2-cell stage embryo. In a more preferred embodiment the 2-cell stage embryo is a xenopus embryo. In another preferred embodiment, the isolated animal pole explant is isolated at the late blastula stage. In a preferred embodiment of this type, the animal pole explant is cultured until the mid-neurula stages.

In one embodiment, the animal pole explant is dissociated for 2 hours after its isolation and then reaggregated prior to its culturing. In a related embodiment the explant is dissociated for 4 hours after isolation and then reaggregated prior to the culturing. In still another embodiment the explant is dissociated for 6 hours after isolation and then reaggregated prior to culturing.

In one embodiment the epidermal marker is epidermal keratin. In another embodiment a neural marker is monitored rather than an epidermial marker. In one such embodiment, the neural marker is NCAM. In still another embodiment, both an epidermal marker and a neural marker are monitored.

Preferably, the assaying of the transcription of the epidermal or neural marker protein is performed with reverse transcriptase polyinerase chain reaction (RT-PCR). Alternatively, the marker transcript can be translated and identified with an antibody. The present invention also envisions marker proteins that are fusion or chimeric proteins which can be identified by their heterologous amino acid sequence, e.g., a FLAG-tag or green fluorescent protein.

The present invention also provides a method of preventing and/or treating cellular debilitations, derangements and/or dysfunctions and/or disease states in vertebrates, preferably maitmmals, more preferably humans, comprising administering to an ainimal a therapeutically effective amount of a material selected from the group consisting of eF-4AIII, an active firagment thereof, an agent capable of promoting the production and/or the activity of eIF-4AIII, an agent capable of mimicking the activity of eIF-4AIII and mixtures thereof, or an agent capable of inhibiting the production of eIF-4AIII and/or a specific binding partner to eIF-4AIII. Such methods take advantage of the property of eIF-4AIII to induce the fonnation of epidermis.

The present invention therefore provides methods of treating cellular debilitations which results from the infliction of wounds, including wounds that result from surgery, or cellular debilitations which result from burns. The methods of the present invention also may be used in disease states in which the foimation of tumors are derived from neural tissue.

The present invention further provides a method for producing artificial skin comprising injecting an amount of eIF-4AIII or active firagment thereof sufficient to form epidermis to culture cells that is thereby induced to form epidermis. In one such embodiment the amount of eIF-4AIII is minimally 5 nanograms per milliliter. Such artificial skin may be used for testing cosmetics or other externally applied medicaments.

The present invention also includes a method of inhibiting neural induction comprising administering to an animal, preferably a vertebrate, more preferably a mammal, and most preferably a human an amount of eIF-4AIII sufficient to inhibit neural induction. In a related embodiment, the inhibition of neural induction is obtained by administering to the nimal an active fragment of eIF-4AIII in sufficient quantity to inhibit neural induction. In yet another embodiment, the method of inhibiting neural induction comprises adinistering to an animal an amount of an agent capable of promoting the production of eIF-4AIII sufficient to inhibit neural induction. In still another embodiment, the present invention provides a method of inhibiting neural induction, that comprises administering to an animal an amount of an agent that mimics the activity of eIF-4AIII that is sufficient to inhibit neural induction. The present invention also includes administering mixtures of these agents, and/or a specific binding partner to eIF-4AIII.

The present invention further includes a method of inducing epidermis formation comprising administering to an animal, preferably a vertebrate, more preferably a mammal, most preferably a human an amount of eIF-4AIII sufficient to induce epidermal formation. In a related embodiment, the inhibition of inducing epide-lrnal formation is obtained by adimnistering to the alimal an amount of an active fiagment of eIF-4AIII sufficient to induce epidermis fomnation. In yet another embodiment, the method of inducing epidermal formation comprises administering to an animal an amount of an agent capable of promoting the production of eIF-4AIII sufficient to induce epidermis formation. In still another embodiment, the present invention provides a method of inducing epidermal formation, that comprises administering to an animal an amount of an agent that mimics the activity of eIF-4AIII that is sufficient to induce epidermis formation. The present invention also includes administering mixtures of these agents.

Accordingly, it is a principal object of the present invention to provide a purified translation initiation factor (eIF-4AIII) which functions in the early development of vertebrate embryos.

It is a further object of the present invention to provide the awmno acid and nucleic acid sequences of xenopus eIF-4AIII.

It is a further object of the present invention to provide an antibody that is specific for eIF-4AIII.

It is a further object of the present invention to provide a method of diagnosing subjects having a pre-cancerous condition related to a mutated eIF-4AIII.

It is a further object of the present invention to provide a method of diagnosing a potential early developmental defect in order to prevent birth defects.

It is a further object of the present invention to provide a method of screeiing drugs to identify a drug that either enhances or diminishes the activity of eIF-4AIII.

These and other aspects of the present invention will be better appreciated by reference to the following drawings and Detailed Description.

BRIEF DESCRIPTION OF THE DRAWINGS

FIGS. 1A–1E show that XeIF-4AIII expression is elevated in the ventral versus dorsal ectoderrn FIGS. 1A–B shows the comparison of the deduced amino acid sequences of XeIF-4AIII and NeIF-4A3. Conserved amino acids are shown in black boxes. FIG. 1E shows the percent identitv between XeIF-4AIII and selected members of the eIF-4A gene family. FIG. 1C shows XeIF-4AIII expression during development. cSRC and EF1-α are used as loading controls. The "-RT" lane contains all reagents except reverse transcriptase and was used as a negative control. FIG. 1D shows XeIF-4AIII expression in imdblastula dorsal and ventral ectodenu explants (stage 11.5). Epidermal keratin expression is restricted to the ventral ectoderm; Xbra, a pan-mesodermal marker at this stage, is absent from the explants. XeIF-4AIII levels in the dorsal and ventral ectodeim were obtained by quantitative phosphorimagilng, with normalization to EF1-α levels [Kindc et al., *Dev. Biol.*, 133:93 (1989)]. RT-PCR wa s performed as described in [Wilson and HeSnmati-Brivarou, 1995, supra]. Primers used ih this study are described in [Hemmati-Brivanlou and Melton, Cell, 77:273 (1994); Hemnati-Brivardou et al., *Cell*, 77:283 (1994)]. Quantitative phosphorimage analysis was perfoeisseed with a Molecular Dysaimics Pheosphordisoager, utilizing the ImageQuaa ut software package.

FIG. 2A shows the induction of epideris by XeIF-4AIII, but not XeIF-4E, in dissociated ectodermn cultures. Synthetic RNA, as fisted, was injected into both blastomeres of 2-cell stage embryos; 2 ng mRNA was injected into each blastomere. Animnal caps were dissected at late blastula stages (stage 9), dissociated for 4 hours, then reaggregated and cultured until midneui-ula stages (stage 20). BMP-4 protein was added to the sample in lane 4 at 2 $\mu$M (50 ng/mfl) immediately after dissociation. EF1-α is used as a loading control. NCAM is a pan-neural marker, and epidermal keratin is a marker of epidermis. Xbra is expressed in both the notochord and ventral/posterior mesoderm at this stage. muscle actin is a marker of mediolateral mesodem-L The "-RT" lane contains all reagents except reverse transcriptase and was used as a negative control. Microinjection, explant dissection, and dissociation cultures were performed as described in [Wilson and Hernnati-Brivanlou, 1995, supra]. FIG. 2B shows that XeIF-4E, but not XeIF-4AIII, induces mesodermn in intact ectodenlm Synthetic RNA, as listed, was injected as in FIG. 2A. Animal caps were dissected at late blastula stages (stage 9), and cultured intact until midgastrula stages (stage 11.5). Xbra is a marker of both notochord and of all non-involuted mesoderm at this stage. FIG. 2C shows the induction of epidermis by XeIF-4AIII, but not MeIF-4AI, in dissociated ectoderm cultures. RNA injection, cell culture, markers, and controls are as in FIG. 2A. For single RNAs, Ing was injected into each blastomere; for double RNAs, 2ng was injected into each blastomere. The protein coding regions of XeIF-4AIII and MeIF-4AI were subcloned into pCS2 [Rupp et al., *Genes and Dev.*, 8:1311 (1994); Turner and Weintraub, *Genes and Dev.*, 8:1434 (1994)]. The coding region of XeIF-4E was sublonled into pSP64T [Krieg and Melton, *Nucl. Acids Res.*, 12:7057 (1984)]. FIG. 2D shows the general translation is not affected by XeIF-4AIII overexpression. 10ng XeIF-4AIII mMRNA was injected into stage V and VI oocytes and cultured in the presence of $^{35}$S-Methionine for 3 days. Oocytes were lysed and this cell fraction was analyzed on 10% acrygesde gels by SDS-PAGE. All sanples were treated with β-mercaptoethaliol.

FIG. 3A shows that epideforal induction by XeIF-4AII requires reaggregation. FIG. 3B shows that the co-injectioni of a truncated BMP receptor (tBR) blocks epidermal induction by XeIF-4AIII. Synthetic RNA, as fisted, was injected into both blastomeres of 2-cell stage embryos. Ainmal caps were dissected at late blastula stages (stage 9), and dissociated. In FIG. 3A, left side, cells were dissociated for 6 hours to late gastrula stages (stage 12.5), at which point RNA was harvested. Cultures maintained as dissociated until midneurula stages (stage 20) have the said expression profile as cultures harvested at late gastrula stages (data not shown). In FIG. 3A, right side, and FIG. 3B, cells were dissociated for 4 hours, then reaggregated and cultured until myidneurula stages. In FIG. 3A, RNA was injected at the concentrations listed. XeIF-4AIII iduces epidermal keratin and inhibits NCAM expression at RNA concentrations down to 1 ng (lanes 9–16). In FIG. 3B, 1 ng of each RNA was injected per blastonVere. Controls are as listed in FIG. 1A.

DETAILED DESCRIPTION OF THE OF THE INVENTION

Figure 2A:
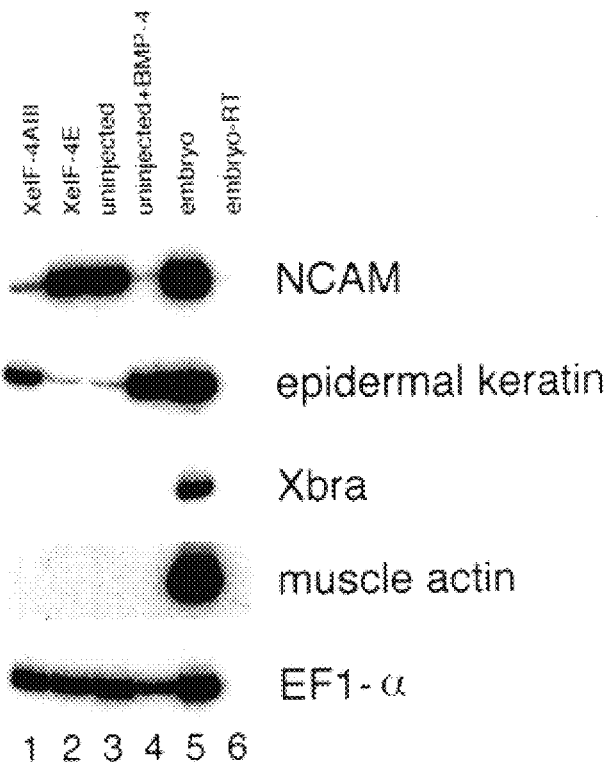
FIGS. 2A–2D deinwonstrate that XeIF-4AIII inhibits neuralization and induces epiderms.

The present invention provides a novel vertebrate translation initiation factor (eIF-4AIII), that plays a role in the differe ntiation of an eibryonic cell to an epidermal cell. Ths divergent -ember of the eIF-4A gene fatily heretofore has only been characterized in plants.

More particularly, as disclosed herein, eIF-4AIII plays a role in a novel translational mechanism which regulates the division of the vertebrate ectoderm into neural and epidermal fates. In dissociated Xenopus ectoderm explants, addition of ectopic Bone Morphogenetic Protein-4 (BMP-4), a potent epideimal inducer and inhibitor of neural fate, leads to an increase in the expression of eIF-4AIII. In the gastrula embryo, Xenopus eIF-4AIII (XeIF-4AIII) expression is elevated in the ventral ectodeim, a site of active BMP signal transduction; moreover, overexpression of XeIF-4AIII induces epidermis in dissociated cells that would otherwise adopt a neural fate, mimicking the effects of BMP-4. XeIF-4AIII-mediated epidermal induction requires an extracellular intermediate as well as an active BMP signaling pathway. Therefore, as disclosed herein BMPs and XeIF-4AIII interact through a positive feedback loop in the ventral ectoderm of the vertebrate gastrula.

As disclosed herein, eIF-4AIII selectively mediates the production of a factor in the epidermal induction pathway that acts, directly or indirectly, upstream of the BMP receptor. Conversely, addition of ectopic BMP-4 stimulates transcription of eIF-4AIII.

The present invention provides the first indication of an animal homolog of eIF-4AIII. Furthermore, the first evidence that a member of the eIF-4A gene family can trigger selective developmental responses is also disclosed. Therefore, agents that serve to modulate eIF-4AIII are useful in selective differentiation of cells to either epidermal or neuronal fates. To this end, the present invention provides drug assays for identifying such agents. In addition, eIF-4AIII itself, or nucleic acids encoding this translation initiation factor, and antibodies raised against eIF-4AIII can be used therapeutically to either enhance or alternatively inhibit the action of this important protein.

Accordingly, one aspect of the present invention provides nucleic acid and aimno acid sequences encoding eIF-4AIII. Another aspect of the present invention provides methods of using the translation initiation factor, nucleic acids encoding the same, and corresponding antibodies and the like for diagnosing, preventing and/or treating cellular debilitation, derangement or dysfunction relating to epidermal cell formation, such as in the treatment of severe bums or wounds, or alternatively relating to neural cell formation, such as in the treatment of Parkinson's disease or other neurologic disorders or in rehabilitative procedures in which neural tissue has been damaged. Similarly, nucleic acids encoding the eIF-4AIll's of the present invention can be used in gene therapy.

Nucleic Acids Peptides and Proteins

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R.I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following telms shall have the definitions set out below.

The terms "transcription initiation factor 4AIII", and "eIF-4AIII" and any variants not specifically listed, may be used herein interchangeably, and as used throughout the present application and claims refer to proteinaceous material including single or multiple proteins, including a dimeric or larger form of the protein and extends to those proteins having the amino acid sequences described herein, and the profile of activities set forth herein. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the protein. Also, the terms "transcription initiation factor 4AIII" and "eIF-4AIII" are intended to include within their scope proteins specifically recited herein as well as all substantially homologous analogs and allelic variations. In a preferred embodiment, the eIF-4AIII is xenopus eIF-4AIII (XeIF-4AIII).

One particular embodiment of the present invention is a xenopus eIF-4AIII having an amino acid sequence of SEQ ID NO:2. Once such eIF-4AIII is encoded by a nucleic acid sequence of SEQ ID NO:1. In another particular embodiment, the eIF-4AIII is a human protein containing an amino acid sequence of SEQ ID NO:4. One such eIF-4AIII is encoded by a nucleic acid sequence of SEQ ID NO:3. In still another embodiment, the human eIF-4AIII contains the amino acid sequence of SEQ ID NO:6. One such eIF-4AIII is encoded by a nucleic acid containing the nucleic acid sequence of SEQ ID NO:5. In still another embodiment, a human eIF-4AIII contains the amino acid sequence of SEQ ID NO:8. One such eIF-4AIII is encoded by a nucleic acid containing the nucleic acid sequence of SEQ ID NO:7. SEQ ID NOs:5 and 7 are nucleic acid sequences that correspond to nuk34 (accession #X79538) and KIAA011 (accession #D21853). Neither of these sequences have heretofore been specifically identified as human eIF-4AIII hoiologs. Furthermore, the present invention includes the use of these specified proteins and nucleic acids in all of the methods and therapies disclosed herein, including for use in making antibodies and in drug development.

The amino acid residues described herein are preferred to be in the "L" isomeric fonlm However, residues in the "D" isomeric form can be substituted for any L-amino acid residue, as long as the desired functional property of the peptide is retained.

A "replicon" is any genetic element (e.g., plasmid, chromosome, virus) that functions as an autonomous unit of DNA replication in vivo; i.e., capable of replication under its own control.

A "vector" is a replicon, such as plasimd, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded fonm or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylationi signals, teiminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defming the present invention, the promoter sequence is bounded at its 3' teiminus by the transcription initiation site and extends upstream (5' direction) to include the minimum number of bases or elements necessary to initiate transcription at levels detectable above background. Within the promoter sequence will be found a transcription initiation site (conveniently defmied by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-teiminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of about 15 or more nucleotides, preferably more than about 24 and more preferably about 36 nucleotides. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the teiplate. For example, a non-complementary nucleotide fiagment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

Mutations can be made in nucleotide sequences of the present invention such that a particular codon is changed to a codon which codes for a different aimno acid. Such a mutation is generally made by making the fewest nucleotide changes possible. A substitution mutation of this sort can be made to change an amino acid in the resulting protein in a non-conservative maimer (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such conservative amino acid changes define the term "a conservative amino acid substitution" as used herein, which is used to denote one or more conservative changes.

A conservative change generally leads to less change in the structure and function of the resulting protein. A non-conservative change is more likely to alter the structure, activity or function of the resulting protein. The present invention should be considered to include all sequences encoding or containing one or more conservative amino acid substitutions which do not significantly alter the activity or binding characteristics of the resulting protein.

The following is one example of various groupings of amino acids:
Amino Acids with Nonpolar R Groups
  Alanine; Valinie; Leucine; Isoleucine; Proline; Phenylalaine; Tryptophan; and Methionine.
Amino Acids with Uncharged Polar R Groups
  Glycine; Serine; Threonine; Cysteine; Tyrosine; Asparagine; and Glutaine.
Amino Acids with Charged Polar R Groups (negatively charged at pH 6.0)
  Aspartic acid and Glutamic acid.
Basic Amino Acids (positively charged at pH 6.0)
  Lysine; Arginine; and Histidine (at pH 6.0)
Particularly preferred conservative substitutions are:
  Lys for Aig and vice versa such that a positive charge may be maintained;
  Glu for Asp and vice versa such that a negative charge may be maintained;
  Ser for Thi such that a free —OH can be maintained; and
  Gln for Asn such that a free $NH_2$ can be maintained.

Amino acid substitutions may also be introduced to substitute an amino acid with a particularly preferable property. For example, a Cys may be introduced to create a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

A "h-eterologous amino acid sequence", as used herein is an amino acid sequence that is the part of a chimeric (or fusion) protein (or peptide) that comprises an eIF-4AIII of the present invention (or a fiagment thereof) which is not part of the naturally occurring eIF-4AIII. The heterologous amino acid sequence can have a regulatory and/or structural property. In one such embodiment, the heterologous amino acid sequence contains a protein (e.g., green fluorescent protein) or peptide (e.g., FLAG) that functions as a means of detecting the chimneric/fusion protein/peptide.

A "heterologous nucleotide sequence" as used herein is a nucleotide sequence that is added to a nucleotide sequence of a eIF-4AIII of the present invention or fragment thereof by recombinant methods to form a nlcleic acid which is not naturally formed in nature. Such nucleic acids can encode an eIF-4AIII protein of the present invention or fragment thereof, and an "heterologous aninio acid sequence" foing a chimeric and/or fusion protein. Such heterologous nucleotide sequences can also comprise non-coding sequences including restriction sites, regulatory sites, promoters and the like. Alternatively, a heterologous nucleotide sequence can contain a non-coding nucleotide sequence which serves as a specific oligonucleotide marker or has a functional property, such a regulatory sequence, e.g., an iron responsive element (IRE), [Theil, *J. Biol. Chem.* 265:4771–4774 (1990); Theil et al., *Biofactors*, 4:8–93 (1993); Klausner et al., *Cell*, 72:19–28 (1993)].

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flaik the mammalian genomic DNA in the genome of the source organisrm Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

"Heterologous DNA" refers to DNA not naturally located in the cell, or in a chromosomal site of the cell. Preferably, the heterologous DNA includes a gene foreign to the cell.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by imitosis. A "cell line" is a clone of a primary cell that is capable of stable growth in vitro for many generations.

As used herein, the terms "restriction endonucleases" and "restriction einymes" refer to bacterial enzymes, each of which cut double-stranded DNA at or near a specific nucleotide sequence.

Two DNA sequences are "substantially homologous" when at least 85% (preferably at least about 90%, and most preferably at least about 95%) of the nucleotides match over the defmied length of the DNA sequences. In one preferred embodiment, there are no gaps in the sequence comparison, i.e., both sequences are strictly aligned without intervening nucleotides being present in one sequence and not the other. Such a preferred embodiment generally describes coding sequences only. Sequences that are substantially homologous can be identified by comparing the sequences using standard software available in sequence data banks, or in a Southern hybridization experiment under, for example, stringent conditions as defined for that particular systenm Defining appropriate hybridization conditions is within the skill of the art. See, e.g., Maniatis et al., supra; DNA Cloning, Vols. I & II, slupra; Nucleic Acid Hybridization, supra.

Likewise, two polypeptide sequences are "substantially homologous" when at least about 80% (preferably at least about 90%, and most preferably at least about 95%) of the amino acids are either identical or contain conservative amino acid changes, as defined above, over the defined length of the polypeptide sequences. Preferably, the similar or homologous sequences are identified by aligiment using, e.g., the GCG pileup program (Genetics Computer Group, Prograrn Manual for the GCG Package, Version 7, Madison Wis.), using the default parameters.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions are used corresponding to 50° C. as described by Church and Gilbert [*Proc. Natl. Acad. Sci. USA*, 81:1991–1995 (1984).] Washes are performed in 2×SSC/0.1% SDS at 50° C. Moderate stringency hybridization conditions correspond to a higher temperature e.g., 60° C. High stringency hybridization conditions are performed at 65° C. Washes in this case are performed in 0.3×SSC/0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of shimarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., suipra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides or more.

In a specific embodiment, the term "standard hybridization conditions" refers to a $T_m$ of 550° C., and utilizes conditions as set forth above. In a preferred embodiment, the $T_m$ is 60° C.; in a more preferred embodiment, the $T_m$ is 65° C.

The term "standard hybridization conditions" refers to salt and temperature conditions substantially equivalent to 5×SSC and 65° C. for both hybridization and wash.

The term "approximately" is used interchangeably with the term "about" and means that the value may vary by 10%, preferably no more than 5%, and most preferably no more than 2%.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading fiame upstream of the DNA sequence.

A gene encoding eIF-4AIII, whether genomic DNA or cDNA, can be isolated from any source, particularly from a human cDNA (or EST) or genomic library. In view and in conjunction with the present teachings, methods well known in the art, as described above can be used for obtaining eIF-4AIII genes from any source (see, e.g., Sambrook et al., 1989, supra).

Accordingly, any animal cell potentially can serve as the nucleic acid source for the molecular cloning of a eIF-4AIII gene. The DNA may be obtained by standard procedures known in the art from cloned DNA (e.g., a DNA "library"), and preferably is obtained from a cDNA library prepared from tissues with high level expression of the protein by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain jitron sequences. Whatever the source, the gene can be molecularly cloned into a suitable vector for propagation of the gene.

In the molecular cloning of the gene from genomic DNA, DNA fragments are generated, some of which will encode the desired gene. The DNA may be cleaved at specific sites using various restriction etizyes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylarnide gel electrophoresis and column chromatography.

Once the DNA fragments are generated, identification of the specific DNA fragment containing the desired eIF-4AIII gene may be accomplished in a number of ways. For example, if an amount of a portion of a eIF-4AIII gene or its specific RNA, or a fragment thereof, is available and can be purified and labeled, the generated DNA fragments may be screened by nucleic acid hybridization to the labeled probe [Benton and Davis, *Science*, 196:180 (1977); Grunistein and Hogness, *Proc. Natl. Acad. Sci. U.S.A.*, 72:3961 (1975)]. For example, a set of oligonucleotides co-responding to the partial aimno acid sequence information obtained for the efF-4AIII protein can be prepared and used as probes for DNA encoding eIF-4AIII, or as primers for cDNA or mRNA (e.g., in combination with a poly-T primer for RT-PCR). Preferably, a fragment is selected that is highly unique to eIF-4AIII of the invention. Those DNA fragments with substantial homology to the probe will hybridize. As noted above, the greater the degree of homology, the more stringent hybridization conditions can be used. In a specific embodiment, high stringency hybridization conditions are used to identify a homologous eIF-4AIII gene.

Further selection can be carried out on the basis of the properties of the gene, e.g., if the gene encodes a protein product having the isoelectric, electrophoretic, aim no acid composition, or partial amino acid sequence of the eIF-4AIII protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for eIF-4AIII.

A eIF-4AIII gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified eIF-4AIII DNA, or may be synthetic oligonucleotides designed from the partial amino acid sequence information. Immunoprecipitation analysis or functional assays (e.g., translation initiation activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against eIF-4AIII.

A radiolabeled eIF-4AIII cDNA can be synthesized using the selected mRNA (from the adsorbed polysomes) as a template. The radiolabeled mRNA or cDNA may then be used as a probe to identify homologous eIF-4AIII DNA fiagments from among other genomic DNA fragments.

The genes encoding eIF-4AIII derivatives and analogs of the invention can be produced by various methods known in the art. The mianipulations which result in their production can occur at the gene or protein level. For example, the cloned eIF-4AIII gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of eIF-4AIII, care should be taken to ensure that the modified gene remains within the same translational reading frame as the eIF-4AIII gene, uninteiiupted by translational stop signals, in the gene region where the desired activity is encoded.

Additionally, the e[F-4AIII-encodiing nucleic acid sequence can be mutated in vitro or in vivo, to create and/or destroy translation, initiation, and/or teliination sequences, or to create variations in coding regions and/or form new restriction endonuclease sites or destroy preexisting ones, to facilitate further in vitro modification. Preferably, such mutations enhance the functional activity of the mutated eIF-4AIII gene product. Any technique for mutagenesis known in the art can be used, including but not limited to, in vitro site-directed mutagenesis [Hutclinson, et al., *J. Biol. Chem.*, 253:6551 (1978); Zoller and Smith, *DNA*, 3:479–488 (1984); Oliphant et al., Gene, 44:177 (1986); Hutchinson et al., *Proc. Natl. Acad. Sci. U.S.A.*, 83:710 (1986)], use of TAB® linkers (Pharmacia), etc. PCR techniques are prefenred for site directed mutagenesis (see Higuchi, 1989, "Using PCR to Enginheer DNA", in *PCR Technology: Principles and Applications for DNA Amplification*, H. Erlich, ed., Stockton Press, Chapter 6, pp. 61–70).

The present invention also relates to cloning vectors containing genes encoding analogs and derivatives of eIF-4AIII of the invention, that have the same or homologous functional activity as eIF-4AIII, and homologs thereof from other species. The production and use of derivatives and analogs related to eIF-4AIII are within the scope of the present invention. In a specific embodiment, the derivative or analog is functionally active, i.e., capable of exhibiting one or more functional activities associated with a full-length, wild-type eIF-4AIII of the invention.

eIF-4AIII derivatives can be made by altering encoding nucleic acid sequences by substitutions, additions or deletions that provide for functionally equivalent molecules.

Preferably, derivatives are made that have enhanced or increased kinase activity relative to native eIF-4AIII.

Due to the degeneracy of nucleotide coding sequences, other DNA sequences which encode substantially the same aimino acid sequence as a eIF-4AIII gene may be used in the practice of the present invention. These include but are not limited to allelic genes, homologous genes from other species. and nucleotide sequences comprising all or portions of eIF-4AIII genes which are altered by the substitution of different codons that encode the same amino acid residue witlin the sequence, thus producing a silent change.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (liikers) onto the DNA termini; these ligated tinkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of orgainism can be prepared for replication in both *E. coli* and *Saccharomyces cerevisiae* by linking sequences from an *E. coli* plasmid with sequences from the yeast 2µ plasmid.

In an alternative method, the desired gene may be identified and isolated after insertion into a suitable cloning vector in a "shot gun" approach. Enrichment for the desired gene, for examnple, by size fractionation, can be done before insertion into the cloning vector.

Expression of eIF-4AIII Polypeptides

The nucleotide sequence coding for eIF-4AIII, or antigenic fragment, derivative or analog thereof, or a functionally active derivative, including a chireric protein, thereof, can be inserted into an appropriate expression vector, i.e., a vector which contains the necessary elements for the trauscription and translation of the inserted protein-coding sequence. Such elements are telmed herein a "promoter." Thus, the nucleic acid encoding the eIF-4AIII of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding eIF-4AIII and/or its flanking regions.

Potential host-vector systems include but are not limited to amtphibian cell systems infected with appropriate viral vectors, or mammalian cell systems infected with virus (e.g., vaccina virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant eIF-4AIII protein of the invention, or functional fragment, derivative, chimeric construct, or analog thereof, may be expressed chromosomally, after integration of the coding sequence by recombination. In this regard, any of a number of amplification systems imnay be used to achieve high levels of stable gene expression (See Sambrook et al., 1989, supra).

The cell containing the recombinant vector comprising the nucleic acid encoding eIF-4AIII is cultured in an appropriate cell culture medium under conditions that provide for expression of eIF-4AIII by the cell.

Any of the methods previously described for the insertion of DNA fragments into a clonig vector may be used to construct expression vectors containing a gene consisting of appropriate transcriptional/translational control signals and the protein coding sequences. These methods may include in vitro recombinant DNA and synthetic techniques and in vivo recombination (genetic recombination). Expression of the eIF-4AIII protein may be controlled by any promoter/ enhanicer element known in the art, but these regulatory elements must be functional in the host selected for expression. Promoters which may be used to control eIF-4AIII gene expression include, but are not limited to, the SV40 early promoter region [Benoist and Chambon, *Nature*, 290:304–310 (1981)], the promoter contained in the 3' long teiminal repeat of Rous sarcoma viius [Yamamoto et al., *Cell*, 22:787–797 (1980)], the herpes thymidine kinase promoter [Wagner et al., *Proc. Nati. Acad. Sci. U.S.A.*, 78:1441–1445 (1981)], the regulatory sequences of the metallothionein gene [Brinster et al., *Nature*, 296:39–42 (1982)]; prokaryotic expression vectors such as the β-lactamase promoter [Villa-Kamaroff et al., *Proc. Natl. Acad. Sci. U.S.A.*, 75:3727–3731 (1978)], or the tac promoter [DeBoer et al., *Proc. Natl. Acad. Sci. U.S.A.*, 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosplhoglycerol kinase) promoter, alkaline phosphatase promoter; and the animal transcriptional control regions, which exhibit tissue specificity and have been utilized in transgellic animals: elastase I gene control region which is active in pancreatic acinar cells [Swift et al., *Cell*, 38:639–646 (1984); Ornitz et al., *Cold Spring Harbor Symp. Quant. Biol.*, 50:399–409 (1986); MacDonald, *Hepatology*, 7:425–515 (1987)]; insulin gene control region which is active in pancreatic beta cells [Hanahan, *Nature*, 315:115–122 (1985)], immunoglobulin gene control region which is active in lyuphoid cells [Grosschedl et al., *Cell*, 38:647–658 (1984); Adames et al., *Nature*, 318:533–538 (1985); Alexander et al., *Mol. Cell. Biol.*, 7:1436–1444 (1987)], mouse mammary tumor virus control region which is active in testicular, breast, lymphoid and mast cells [Leder et al., *Cell*, 45:485–495 (1986)], albumin gene control region which is active in liver [Phikert et al., *Genes and Devel.*, 1:268–276 (1987)], alpha-fetoprotein gene control region which is active in liver [Kiumlauf et al., *Mol. Cell. Biol.*, 5:1639–1648 (1985); Hammer et al., *Science*, 235:53–58 (1987)], alpha 1-antitrypsin gene control region which is active in the liver IKelsey et al., *Genes and Devel.*, 1:161–171 (1987)], beta-globin gene control region which is active in myeloid cells [Mogram et al., *Nature*, 315:338–340 (1985); Kollias et al., *Cell*, 46:89–94 (1986)], myelin basic protein gene control region which is active in oligodendrocyte cells in the brain [Readhead et al., *Cell*, 48:703–712 (1987)], myosin light chain-2 gene control region which is active in skeletal muscle [Sani, *Nature*, 314:283–286 (1985)], and gonadotropic releasing hormone gene control region which is active in the hypothalamus [Mason et al., *Science*, 234:1372–1378 (1986)].

Expression vectors containing a nucleic acid encoding a eIF-4AIII of the invention can be identified by a number of approaches including: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transfoimation phenotype, occlusion body formation in baculovirus, etc.) caused by the insertion of foreign genes in the vector. In another example, if the nucleic acid encoding eIF-4AIII is inserted within the "selection marker" gene sequence of the vector, recombinants containing the eIF-4AIII insert can be identified by the absence of the marker gene function. In the fourth approach, recombinant expression vectors can be identified by assaying for the activity, biochemical, or imunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and Synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phage λ, e.g., NM989, and other phage DNA, e.g., M13 and Filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasiids that have been modified to employ phage DNA or other expression control sequences; and the like.

Any of a wide variety of expression control sequences— sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the tip system, the TAC systei, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression systerm However, one skilled in the art will be able to select the proper vectors, expression control sequences, and hosts without undue experimentation to accomplish the desired expression without departing firom the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

In a specific embodiment, an eIF-4AIII fusion protein or peptide can be expressed. A eIF-4AIII fusion protein comprises at least a functionally active portion of a non-eIF-4AIII protein joined via a peptide bond to a eIF-4AIII or a fiagment of a eIF-4AIII. Similarly a eIF-4AIII fusion peptide can be expressed. The non-eIF-4AIII sequences can be amnino- or carboxyl-telminal to the eIF-4AIII sequences. For stable expression of a eIF-4AIII fusion protein, the portion of the non-eIF-4AIII fusion protein or peptide can be joined via a peptide bond to the amino terminus of the eIF-4AIII protein. A recombinant DNA molecule encoding such a fusion protein comprises a sequence encoding at a functionally active portion of a non-eIF-4AIII protein or peptide joined in-fiame to the eIF-4AIII coding sequence, and preferably encodes a cleavage site for a specific protease, e.g., troimbin or Factor Xa, preferably at the eIF-4AIII-non-eIF-4AIII juncture. Such a cleavage site can be used in the ultimate purification of the eIF-4AIII, e.g., when the heterologous amino acid sequence portion of the fusion protein is used as a ligand for an affinity column.

In a specific embodiment, the fusion protein is expressed in *Escherichia coli*. An example of a fusion peptide is a eIF-4AIII having a FLAG-tag. An example of a fusion protein is a eIF-4AIII or a fragment thereof joined with a green fluorescent protein or modified green fluorescent protein as described in U.S. Pat. No. 5,625,048, Issued Apr. 29, 1997 herein incorporated by reference in its entirety. Such fusion proteins and peptides may also be classified as chimeric proteins or peptides.

It is further intended that eIF-4AIII analogs may be prepared from nucleotide sequences of the protein complex/subunit derived within the scope of the present invention. Analogs, such as fragments, may be produced, for exaimnple, by pepsin digestion of eIF-4AIII material. Other analogs, such as muteins, can be produced by standard site-directed mutagenesis of eIF-4AIII coding sequences. Analogs exliibiting "eIF-4AIII activity" such as small molecules, whether functioning as promoters or inhibitors, may be identified by known in vivo and/or in vitro assays.

As mentioned above, a DNA sequence encoding a eIF-4AIII can be prepared synthetically rather than cloned. Thie DNA sequence can be designed with the appropriate codons for the eIF-4AIII amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express eIF-4AIII analogs or "muteins". Alternatively, DNA encoding muteins can be made by site-directed mutagenesis of native eIF-4AIII genes or cDNAs, and muteins can be made directly using conventional polypeptide synthesis.

A general method for site-specific incorporation of unnatural amino acids into proteins is described in Chruistopher J. Noren, Spencer J. Anthony-Cahill, Michael C. Griffith, Peter G. Schultz, Science, 244:182–188 (April 1989). This method may be used to create analogs with unnatural amino acids.

Antibodies

An "antibody" is any immunoglobulin, including antibodies and fragments thereof, that binds a specific epitope. The teii encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical foiis as used herein contemplates both an intact immunoglobulin molecule and an immunologically active portion of an immunoglobulin molecule.

Exemplary antibody molecules are intact irmnunoglobulin molecules, substantially intact immunoglobulin molecules and those portions of an immunloglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is prefelred herein.

The phrase "monoclonal antibody" in its various grammatical foinis refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The general methodology for making monoclonal antibodies by hybridomas is well known. Immortal, antibody-producing cell lines can also be created by techniques other than fusion, such as direct transfoimation of B lymphocytes with oncogenic DNA, or transfection with Epstein-Barr virus. See, e.g., M. Schreier et al., "Hybridoma Techniques" (1980); Haimerling et al., "Monoclonal Antibodies And T-cell Hybridoinas" (1981); Kenniett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against eIF-4AIII peptides can be screened for various properties; i.e., isotype, epitope, affinity, etc. Of particular interest are monoclonal antibodies that neutralize the binding activity of the eIF-4AIII or its subunits. Such monoclonals can be readilv identified in, for example, gel-shift assays. High affinity antibodies are also useful when immunoaftfiity purification of native or recombinant eIF-4AIII is possible.

Preferably, the anti-eIF-4AIII antibody used in the diagnostic methods of this invention is an affniity purified polyclonal antibody. More preferably, the antibody is a monoclonal antibody (mAb). In addition, it is preferable for the anti-eIF-4AIII antibody molecules used herein be in the form of Fab, Fab', F(ab')$_2$ or F(v) portions of whole antibody molecules.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in Antibodies—A Laboratoiy Manual, Harlow and Lane, eds., Cold Spring Harbor Laboratory, New York (1988), which is incorporated herein by reference. Briefly, to foim the hybridoma from which the monoclonal antibody composition is produced, a myeloma or other self-perpetuating cell line is fused with lymphocytes obtained from the spleen of a maimal hyperirm-nunized with a eIF-4AIII-binding portion thereof, or eIF-4AIII, or a DNA-binding portion thereof.

Splenocytes are typically fused with myeloma cells using polyethylene glycol (PEG) 6000. Fused hybrids can be selected by their sensitivity to HAT. Hybridomas producing a monoclonal antibody useful in practicing this invention are identified by their ability to immunoreact with the present eIF-4AIII.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the mediuim The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Methods for producing monoclonal anti-eIlF-4AIII antibodies are also well-known in the art. See Nimran et al., Proc. Natl. Acad. Sci. USA, 80:4949–4953 (1983). Typically, the present eIF-4AIII or a peptide analog is used either alone or conjugated to an immunogenic carrier, as the immunogen in the before-described procedure for producing anti-eIF-4AIII monoclonal antibodies. The hybridomas are screened for the ability to produce an antibody that irrunoreacts with the eIF-4AIII peptide analog and the eIF-4AIII of the present invention.

Diagnostics and Therapeutics

The phirase "phaimaceutically acceptable" refers to molecular entities and compositions that are physiologically tolerable and do not typically produce an allergic or similar untoward reaction, such as gastric upset, dizziness and the like, when administered to a human.

The phruase "therapeutically effective amount" is used herein to mean an amount sufficient to significantly ameliorate a symptom caused by an abnormal eIF-4AIII, or a deficiency/overexpression of eIF-4AIII (e.g., a 20% improvement).

The possibilities both diagnostic and therapeutic that are raised by the existence of the eIF-4AIII, derive from the fact that the eIF-4AIII is a member of the class of proteins involved in translation initiation and futhermore plays an important role in signal transduction in the embryogenesis. As suggested earlier and elaborated further on herein, the present invention contemplates phaimaceutical intervention in the cascade of events in which the eIF-4AIII of the present invention is implicated, to modulate the activity mediated by this important signal transducer.

As discussed earlier, the eIF-4AIIIs of the present invention or their binding partners or other ligands or agents exhibiting either mimicry or antagonism to the eIF-4AIII or control over their production, may be prepared in pharmaceutical compositions, with a suitable carrier and at a strength effective for administration by various means to a patient experiencing an adverse medical condition associated with the abnormal expression of eIF-4AIII for the treatment thereof. A variety of administrative techniques may be utilized, among them topological, or alternatively parenteral techniques such as subcutaneous, intravenous and intraperitonieal injections, catheterizations and the like. Average quantities of the eIF-4AIIIs may vary and in particular should be based upon the recommendations and prescription of a qualified physician or veterinarian.

Also, antibodies including both polyclonal and monoclonal antibodies, and drugs that modulate the production or activity of the eIF-4AIIIs of the present invention may possess certain diagnostic applications and may for example, be utilized for the purpose of detecting and/or measuring genetic pre-conditions (e.g. pre-cancerous conditions). For example, the eIF-4AIIIs of the present invention or its structural/functional domains may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the eIF-4AIII of the invention may be discovered or synthesized, and may be used in diagnostic and/or therapeutic protocols.

As suggested earlier, the diagnostic method of the present invention comprises examining a cellular sample or medium by means of an assay including an effective amount of an antagonist to a eIF-4AIII protein, such as an anti-eIF-4AIII antibody, preferably an affinity-purified polyclonal antibody, and more preferably a mAb. In addition, it is preferable for the anti-eIF-4AIII antibody molecules used herein be in the form of Fab, Fab', F(ab')$_2$ or F(v) portions or whole antibody molecules. Methods for isolating and inducing anti-eIF-4AIII antibodies and for determinig and optimizing the ability of anti-eIF-4AIII antibodies to assist in the examination of the target cells are all well-known in the art.

The present invention further contemplates therapeutic compositions useful in practicing the therapeutic methods of this invention. A subject therapeutic composition includes, in admixture, a pharmaceutically acceptable excipient (carrier) and one or more of a eIF-4AIII of the present invention, polypeptide analog thereof or fiagment thereof, as described herein as an active ingredient. In a preferred embodiment, the composition comprises an antigen capable of modulating the specific binding of eIF-4AIII within a target cell.

The preparation of therapeutic compositions which contain polypeptides, analogs or active firagments as active ingredients is well understood in the art. Typically, such compositions are prepared as topological agents or alternatively as injectables, either as liquid solutions or suspensions, however, solid forms suitable for solution in, or suspension in liquid prior to injection (or topological administration) can also be prepared. The preparation can also be emulsified. The active therapeutic ingredient is often mixed with excipients winch are pharmaceutically acceptable and compatible with the active ingredient. Suitable excipients are, for example, distilled water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt fonrs. Pharmaceutically acceptable salts include the acid addition salts (formed with the free aio groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodiuim potassium, ammonium, calciui, or fellic hydroxides, and such organic bases as isopropylamine, trimethylamine, 2-ethylaimno ethanol, listidine, procaine, and the like.

The therapeutic polypeptide-, analog- or active fragment-conitaining compositions are conventionally administered topologically or alternatively, intravenously as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manier compatible with the dosage formulation, and in a therapeutically effective amount. The quantity to be administered depends on the subject to be treated, capacity of the subject's immiune system to utilize the active ingredient, and degree of inhibition or neutralization of eIF-4AIII desired. Precise amounts of active ingredient required to be admnistered depend on the judgment of the practitioner and are peculiar to each individual. However, suitable dosages may range from about 0.1 to 20, preferably about 0.5 to about 10, and more preferably one to several, micrograims of active ingredient per kilogram body weight of individual per day and depend on the route of adimnistration. Suitable regimes for initial administration and booster shots are also variable, but are typified by an initial admnistration followed by repeated doses at one or more hour intervals by a subsequent injection or other administration.

The present invention also relates to a variety of diagnostic applications, including methods for detecting the presence of stimuli such as the earlier referenced polypeptide ligands, by reference to their ability to elicit the activities which are mediated by the eIF-4AIIIs of the present invention. As mentioned earlier, the eIF-4AIIIs of the present inventions can be used to produce antibodies to itself by a variety of known techniques, and such antibodies could then be isolated and utilized as in tests for the presence of particular activity of eIF-4AIII in suspect target cells.

Assays for Agonists and Aintagonists of eIF-4AIIIs and Kits

Identification and isolation of a gene encoding a eIF-4AIII of the invention provides for expression of eIF-4AIII in quantities greater than can be isolated from natural sources, or in indicator cells that are specially engineered to indicate the activity of eIF-4AIII expressed after transfection or transformation of the cells. Accordingly, in addition to rational design of agonists and antagonists based on the structure of the eIF-4AIII of the present invention, the present invention further contemplates an alternative method for identifying specific ligands of eIF-4AIII using various screening assays known in the art.

Any screening technique known in the art can be used to screen for eIF-4AIII agonists or antagonists. The present invention contemplates screens for small molecules that bind to the eIF-4AIIs of the present invention and agonize or antagonize eIF-4AIII in vitro and/or in vivo. For example, natural products libraries can be screened using assays of the invention for molecules that agonize or antagonize the activity of eIF-4AIII.

Knowledge of the primary sequence of the eIF-4AIIIs of the present invention, and the simllarity of that sequence with other translation initiation factors, can provide an initial clue as to the likely structural properties for an inhibitor or antagonist of eIF-4AIII. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method"[Scott and Smith, 1990, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued December 1986] and Rutter etal. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for eIF-4AIII ligands (e.g., binding partners) according to the present invention.

Screening can be performed with recombinant cells that express the eIF-4AIIIs of the present invention, or alternatively, using purified protein, and/or specific structural/functional domains of the eIF-4AIIIs e.g., produced recombinantly, as described above. For example, a labeled eIF-4AIII can be used to screen libraries, as described in the foregoing references for small molecules that will inhibit the translation initiation activity of eIF-4AIII.

The effective peptide(s) can be synthesized in large quantities for use in in vivo models and eventually in humans to modulate eIF-4AIII signal transduction. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [PatalToyo, Vaccine 10:175–178 (1990)].

In one such embodiment a potential antagonist to an eIF-4AIII of the present invention can be added to a protein synthesis assay in which the eIF-4AIII is a rate lmiting factor. A measure of protein synthesis is determined, and a potential agonist that inhibits that measure of protein synthesis is selected as a potential drug. The protein synthesis assay can be an in vitro, in situ or in vivo assay, but is preferably an in vitro assay. In one such embodiment of this type the assay is performed in a rabbit reticulocyte lysate using a capped mRNA encoding a marker protein.

A "proteins synthesis assay" as used herein is an assay that can be performed in vitro, in situ (i.e., in an isolated cell) or in vivo in which "a measure of protein synthesis" can be determined. One simple assay is the use of an in vitro translation systeim This can be a nuclease-treated reticulocyte lysate, or nuclease-treated translation extract prepared from nucleated cells (such as HeLa cells or Krebs II ascites). In these systems, exogenously added capped mRNA (synthesized in vitro in presence of a cap analog such as m$^7$GpppG) is allowed to be translated in presence of [35S] methionine and the potential antagonist. Added mRNA can be monocistronic (i.e. giving only one gene product) or bicistronic (encoding for two proteins). In the later, the DNA construct is built in such a way that the first cistron will be translated thlough a process called internal initiation [Belshaw et al., *Microbial. Rev.*, 60:499–511 (1996)]. Therefore, comparing the translation of the first cistron (cap-dependent) versus the translation of the second cistron (cap-independent) gives an indication of the specific effects of eIF-4AIII and the cap-dependent machinery. One such mRNA is CAT/EMC/LUC (chlorarnphicol acetyl transferase), followed by sequences directing internal initiation, followed by the reporter gene. Chloramplhenlicol acetyl transferase (CAT) and luciferase (LUC) activity can be monitored by standard methods. Alteinatively, cells can be incubated in presence of 135SI methionine and the total incorporation of the radioactive label in proteins can be monitored. Cultured cell lines, such as HeLa cells or NIH 3T3 cells, are most suitable for the measure of protein synthesis via transfection of a reporter, since they are efficiently translated. [35S] labeling can be done on transformed or primary cells.

A "measure of protein synthesis" as used herein is any determination that can be made in which the synthesis of at least one protein can detected. One such measure is the detection of the amount of synthesis of a specific marker protein, e.g., measuring in vitro translation initiation activity in a rabbit reticulocyte lysate using a capped mRNA marker protein [described in Svitkin et al., *EMBO J.*, 15:7147–7155 (1996)] such as a capped chioramphenicol acetyl transferase (CAT) RNA. Analogous assays may be performed in situ with cells transfected with a nucleic and encoding such a marker protein In one embodiment the cell is a eukaryotic cell, including a yeast cell. In preferred embodiments the cell is a vertebrate cell. In more preferred embodiments the cell is a mamimalian cell. In the most preferred embodiment the cell is a human cell. In one particular embodiment of this type, the potential drug is adinistered into an animal subject.

A "rate-limiting factor" as used herein is a protein required for translation initiation in a cell and/or protein assay in which the rate of translation of at least one mRNA present in the cell and/or protein assay is dependent on the concentration of the functional "rate limiting factor". Therefore, inhibiting a rate limiting factor results in a corresponding decrease in the rate of translation of at least one mRNA present in the cell and/or protein assay.

In a further embodiment of this invention, commercial test kits suitable for use by a medical specialist may be prepared to determine the presence or absence of eIF-4AIII activity in suspected target cells. In accordance with the testing teclhniques discussed above, one class of such kits will contain at least a labeled eIF-4AIII of the present invention or its binding partner, for instance an antibody specific thereto, and preferably directions, and protocols, depending upon the method selected, e.g., "competitive", "sandwich", "DASP" and the like. The kits may also contain peripheral reagents such as buffers, stabilizers, etc.

Accordingly, a test kit may be prepared for the demonstration of the presence of eIF-4AIII, or a nucleic acid encoding a eIF-4AIII comprising:

(a) a predetermined amount of at least one labeled immunocheimcally reactive component obtained by the direct or indirect attachmnent of an eIF-4AIII of the present invention to a detectable label, or alternatively, a labeled anti-eIF-4AIII antibody, or a labeled nucleic acid probe which can hybridize to a nucleic acid encoding a eIF-4AIII with specificity; Preferably, (b) other reagents; directions for use of the kit can also be included.

In one particular embodiment, the diagnostic test kit may comprise:

(a) a known amount of the eIF-4AIII as described above (or a binding partner such as an anti-eIF-4AIII antibody) generally bound to a solid phase to form an immunosorbent, or in the alternative, bound to a suitable tag, or plural such end products, etc. (or their binding partners) one of each;

(b) if necessary, other reagents; directions for use of the test kit can also be provided.

In a further variation, the test kit may be prepared and used for the purposes stated above, wlhch operates according to a predetermined protocol (e.g. "competitive", "sandwich", "double antibody", etc.), and comprises:

(a) a labeled component which has been obtained by coupling eIF-4AIII to a detectable label;

(b) one or more additional immunocheimcal reagents of which at least one reagent is a ligand or an immobilized ligand, selected from the group consisting of:

(i) a ligand capable of binding with the labeled component of (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; again directions can be provided for the performance of a protocol for the detection and/or detefmination of one or more components of an immn nocheilical reaction between eIF-4AIII and a specific binding partner thereto.

In accordance with the above, an assay system for screening potential drugs effective to modulate the activity of the eIF-4AIIIs of the present invention may also be prepared. In one such method a potential diug that modulates the ability of an eIF-4AIII of the present invention to induce the epidermal foimation is identified. First an mRNA encoding the eIF-4AIII is injected into an animal pole of a 2-cell stage embryo in the presence of an agent (i.e., a potential drug). Next the animal pole explant is isolated at the late blastula stage. The animal pole explant is then cultured until midneuw-ula stage. After extracting the RNA from the animal pole explant the transcription of an epideimal marker protein is assayed. By comparing the amount of transcription in the presence of the agent relative to in its absence, an agent is identified as a potential drug when the agent enhances or dlimishes the transcription relative to in its absence. The assaying of the transcription of the epidermal marker may be peiformed by any of a number of means but is preferably deteimined by reverse transcriptase polynerase chain reaction (RT-PCR). In one such embodiment the 2-cell stage embryo is a xenopus embryo. In a preferred embodiment, the animal pole extract is dissociated for two to six hours, preferably four hours, and then reaggregated prior to culturing the animal pole explant until midneurala stage. One such epidelmal marker is epidermal keratin. Similarly, the decrease in neuronal marker protein such as NCAM can also be used to show the epideinal inducement by eIF-4AIII.

Labels

The eIF-4AIIIs of the present inventions, fragments thereof, and their antibodies, nucleic acids encoding the eIF-4AIIIs, the specific domains of eIF-4AIIIs, and probes to the nucleic acids may all be labeled The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamiiie, auramilne, Texas Red, AMCA blue and Lucifer Yellow. A particular detecting material is anti-rabbit antibody prepared in goats and conjugated with fluorescein through an isothiocyaniate.

The eIF-4AIIIs of the present invention or its binding palrtner(s) can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$RE.

Enzyme labels are likewise useful, and can be detected by any of the presently utilized calorimetric, spectrophotometric, fluorospectrophotometric, amperoimetric or gasometric techniiques. The enzyme is conjugated to the selected particle by reaction with bridging molecules such as carbodjirnides, diisocyanates, glutaraldehyde and the like. Many enzymes which can be used in these procedures are known and can be utilized. The preferred are peroxidase, β-glucuromidase, β-D-glucosidase, β-D-galactosidase, urease, glucose oxidase plus peroxidase and alkaline phosphatase. U.S. Pat. Nos. 3,654,090; 3,850,752; and 4,016,043 are refelred to by way of example for their disclosure of alternate labeling material and methods. In addition, green fluorescent protein and derivatives thereof, as exemplified in U.S. Pat. No. 5,625,048 Issued Apr. 29, 1997 and International Publication No: WO 97/26333, hereby incolporated by reference in their entireties, can also be used.

Antisense Gene Targeting and Ribozymes

The functional activity of eIF-4AIII can be evaluated transgeiuically. In this respect, a transgenic mouse model can be used. The eIF-4AIII gene can be used in complementation studies employing transgeiic mice. Transgenic vectors, including viral vectors, or cosmid clones (or phage clones) corresponding to the wild type locus of candidate gene, can be constructed using the isolated eIF-4AIII gene. Cosmids may be introduced into transgenic mice using published procedures [Jaenisch, Science, 240:1468–1474 (1988)]. In a genetic sense, the transgene acts as a suppressor mutation.

Alternatively, a transgenic animal model can be prepared in which expression of the eIF-4AIII gene is disrupted. Gene expression is disrupted, according to the invention, when no functional protein is expressed. One standard method to evaluate the phenotypic effect of a gene product is to employ knock-out technology to delete the gene (see U.S. Pat. No. 5,464,764 Issued Nov. 7, 1995 herein incorporated by reference in its entirety.)

The present invention also extends to the preparation of antisense nucleotides and ribozyies that may be used to inteifere with the expression of the eIF-4AIIIs of the present invention at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, Sci. Amer. 262:40–46 (1990); Marcus-Sekura, Nucl. Acid Res, 15: 5749–5763 (1987); Marcus-Sekura Anal.Biochem., 172:289–295 (1988); Brysch et al., Cell Mol. Neurobiol., 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient. Antisense methods have been used to inhibit the expression of many genes in vitro [Marcus-Sekura, Anal.Biochem., 172:289–295 (1988); Hambor et al., Proc. Natl. Acad. Sci. U.S.A. 85:4010–4014 (1988)] and in situ [Arima et al., Antisense Nuci. Acid Drug Dev. 8:319–327 (1998); Hou et al., Antisense Nucl. Acid Drug Dev. 8:295–308 (1998)].

Ribozymes are RNA molecules possessing the ability to specifically cleave other single stranded RNA molecules in a ianner somewhat analogous to DNA restriction endonucleases. Ribozyies were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, JAMA, 260:3030–3034 (1988); Cech, Biochem. Intl, 18:7–14 (1989)]. Because they are sequence-specific, only mRNAs with particular sequences are inactivated.

Investigators have identified two types of ribozymes, Tetrahymena-type and "harnmerhead"-type [Haselhoff and Gerlach, Nature 334:585–591 (1988)]. Tetrahymena-type ribozymes recognize four-base sequences, while "harnmerhead"-type recognize eleven- to eighteen-base sequences. The longer the recognition sequence, the more likely it is to occur exclusively in the target mRNA species. Therefore, hatmmerhead-type ribozymes are preferable to Tetrahymena-type ribozymes for inactivating a specific mRNA species, and eighteen base recognition sequences are preferable to shorter recogrition sequences.

The DNA sequences described herein may thus be used to prepare antisense molecules against, and ribozymes that cleave mRNAs encoding the eIF-4AIIIs of the present invention.

Gene Therapy and Transaeiiic Vectors

In one embodiment, a gene encoding an eIF-4AIII of the present invention is introduced in vivo in a viral vector. Such vectors include an attenuated or defective DNA virus or RNA virus, such as but not limited to herpes simplex virus (HSV), papillomavirus, Epstein Barr virus (EBV), adenovirus, adeno-associated virus (AAV) human immunodeficiency virus (HIV), simian immunodeficiency virus (SIV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector [Kaplitt et al., Molec. Cell. Neurosci. 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as inteileukii-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Manin et al., 1983, Cell 33:153; Temin et al., U.S. Pat. No. 4,650,764; Temin et al., U.S. Pat. No. 4,980,289; Markowitz et al., 1988, J. Virol. 62:1120; Teiiin et al., U.S. Pat. No. 5,124,263; International Pat. Publication No. WO 95/07358, published Mar. 16, 1995, by Dougherty et al.; and Kuo et al., 1993, Blood 82:845.

Targeted gene delivery is described in International Pat. Publication WO 95/28494, published October 1995.

Alternatively, the vector can be introduced in vivo by lipofection. For the past decade, there has been increasing use of liposomes for encapsulation and transfection of nucleic acids in vitro. Synthetic catiollic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of tipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the eIF-4AIIls of the present invention inserted in the vector. That is, a specific expression vector of the present invention can be used in gene therapy.

Such an expression vector is particularly useful to regulate expression of a therapeutic eIF-4AIII gene. In one embodiment, the present invention contemplates constitutive expression of the eIF-4AIII gene, even if at low levels.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

A POSITIVE RELEGATORY LOOP LINKING BMP AND TRANSLATION INITIATION FACTOR 4AIII

Methods

Construction of libraries from dissociated cells cultured with or without BMP-4, using a reverse-transcrintion PCR-based strategy. Twenty animal cap explants were dissociated and cultured for 4 hours in the presence or absence of 100 ng/ml BMP-4 [Wilson et al., *Nature* 376:331 (1995)]. Parallel cultures were incubated until control embryos reached stage 19, and assayed for the expression of neural and epidermal markers, with results as expected. RNA was extracted as described in [Wilson et al., *Nature* 376:331 (1995)]. One-twentieth of this RNA was used as source material for a subtractive screen. Reverse transcription, Polyierase Chain Reaction (RT-PCR), library construction and screening was performed using a modified protocol originally described previously [Dulac et al., *Cell* 83:195 (1995)]. Briefly, RNA was derived from cells cultured in the presence or absence of BMP-4 and used to generate first strand cDNAs, under conditions favoring uniformly-sized molecules. cDNA libraries were constructed from the two pools and plated at 500 plaques/plate. Two radiolabeled probes were made from the remainder of the cDNA reactions, and used to screen one set of lifts from each library. A total of 5,000 plaques from each pool were screened. Ten clones were isolated that hybridized more strongly to radiolabeled probes generated from the BMP-4 pool. Two of ten plaques showed high identity to NeIF-4AIII [Owttrim et al., *Nucl. Acids Res.* 19:5491 (1991)].

Isolation offull-length cDNA using partial cDNAs as probes. $10^6$ plaques firom a IZapll stage 28 Xenopus head cDNA library [A. Hennati-Brivanlou et al., Development 111:715 (1991)] were screened at high stringency using radiolabelled probes generated from the two isolates described which showed high identity to NeIF-4AIII (described above and below), and a partial clone was obtained (4A-3). PCR amplification of an oocyte cDNA library, using an internal 4A-3 oligo and an oligo derived from the Zap plasmid, was used to isolate the remnaining 5' sequences. cDNAs were sequenced by the dideoxy-chain termination method [F. Sanger, et al., *Proc. Natl. Acad. Sci. USA* 74, 5463 (1977)]. Sequence analysis was carried out using the DNA Strider and DNA Star software packages and the NIH BLAST program.

Construction of Primers: Primers constructed for this study are as follows:
XeIF-4AIII: U:5'-GGGTGTTGCCATTAACTTTGTC;
D:5'-CCTGCCACATGAAATCCTGG. cSRC:
U:5'-GAGTCGCAGTCTGGATATTGC; D:5'-TGGAATGTAGCCAGTCTGCC.

All other primer sequences are listed in [Wilson et al., *Nature* 376:331 (1995); Henmnati-Brivanlou et al., *Cell* 77:273 (1994); and Heimati-Brivanlou et al., *Cell* 77, 283

(1994)]. All reactions were performed for 25 cycles except for EFJ-α, muscle actin, and XeIF-4AIII, which were performed for 21 cycles.

Results

To identify factors involved in epidemnal induction downstream of BMP-4, late blastula animal cap explants were dissociated in the absence or presence of 4 μM BMP-4. Libraries were constructed from dissociated cells cultured with or without BMP-4, using a reverse-transcription PCR-based strategy [Dulac et al., Cell, 83:195 (1995)]. Ten clones whose expression were elevated in the presence of BMP-4 were selected for sequence analysis. Two of the ten showed highest homology to distinct regions of Nicotiana plumbaginifolia (tobacco) eukaryotic Initiation Factor 4A3 (NeIF-4A3) [Owttrim et al., Nucl. Acids Res., 19:5491 (1991)]. These partial cDNAs were used as probes in subsequent library screens to isolate a full-length cDNA [Hemmati-Brivanlou et al., Development, 111:715 (1991); Sanger et al., Proc. Natl. Acad. Sci. USA, 74:5463 (1977)]. This clone shares higher identity (73%) with the tobacco gene than with other vertebrate 4A family members (64% and 66% identity with murine efF-4AI and eIF-4AII, respectively) [Nielson et al., Nucl. Acids Res., 13:6867 (1985); Nielson and Traclisel, EMBO J., 7:2097 (1988)]; therefore, it has been termed "XeIF-4AIII" (FIGS. 1A–1B and 1E).

To determine the expression of XeIF-4AIII during the period in which ectodenn is competent to differentiate into either neural tissue or epidermis, an RT-PCR analysis was performed on embryos harvested between blastula and neural plate stages (FIG. 1C). While expression can be detected at all stages assayed, XeIF-4AIII expression increases dramatically after the midblastula transition (MBT, stage 9.5), the initiation of zygotic transcription.

In the initial differential screen, XeIF-4AIII transcripts, although present in all samples, were elevated in the presence of BMP-4. In separate dissociation experiments, XeIF-4AIII transcripts were elevated 2.5-fold in cells dissociated in the presence of BMP-4. In the gastrula-stage embryo, BMP signaling, and consequently epidermal induction, is thought to occur in the ventral ectodelm; in the dorsal ectoderm, BMP signaling is blocked by secreted factors from Spemann's organizer [Weinstein and Hemmati-Brivainlou, 1997, supra]. In order to examine the localization of XeIF-4AIII expression in the ectodeim duiing gastrula stages, midgastrula dorsal and ventral ectodeim explants were isolated (FIG. 1D). Epidermal keratin, a marker of epidermis, was detected in the ventral explants only [Jonas et al., Proc. Natl. Acad. Sci. USA, 82:5413 (1985)]. While XeIF-4AIII is expressed throughout the midgastrula ectocderm, phosphorimaging data indicated that XeIF-4AIII transcripts are 2-fold more abundant in ventral versus dorsal ectodeim (FIG. 1C). This result is consistent with the present data from dissociated cell cultures, in that active BMP signaling correlates with elevated levels of XeTF-4AIII transcript.

In order to examine the function of XeIF-4AIII, dissociated ectodeim experiments were peiformed on embryos injected with synthetic XeIF-4AIII RNA. Cells were reaggregated at midgastula stages and cultured until midneurula stages. RNA was extracted, and assayed for expression of cell-type specific molecular markers by RT-PCR. Cells from control embryos dissociated in this manner show strong expression of the general neural marker NCAM, and low expression of epidermal keratin, indicating that these cells have neuralized (FIG. 2A, lane 3) [Jonas et al., 1985, supra; Kintner et al., Development, 99:311 (1987)]. Cells dissociated in the presence of BMP-4 express high levels of epidermal keratin, and low levels of NCAM (FIG. 2A, lane 4), indicating their differentiation into epidermis. Like cells treated with BMP-4, cells that express ectopic XeIF-4AIII do not express NCAM, and express high levels of epidermal keratin (FIG. 2A, lane 1). Thus, XeIF-4AIII can induce epidermis in dissociated cells, and inhibit the neural fate. Mesoderm is not present or induced in these cultures: neither muscle actin, a marker of dorsolateral mesodeini, nor Xbra, a marker of both notochord and ventral/posterior meisodeim at this stage, are expressed [Mohun et al., Nature, 311:716 (1984); Smith et al., Cell, 67:79 (1981)].

Figure 2B:
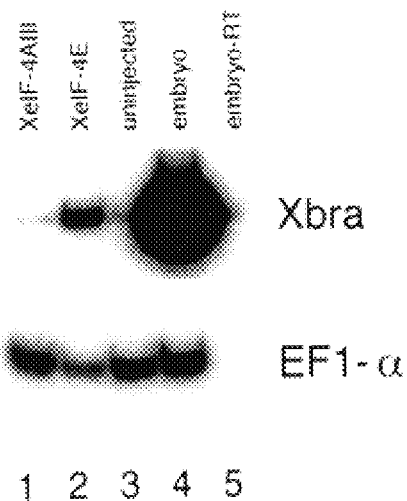

Another component of the translation initiation machinery has also been shown to affect cell fate in the Xenopus ectodeni: eIF-4E overexpression induces mesodeim in intact caps [Klein et al., 1994, supra] (FIG. 2B, lane 2). However, the inductive capacities of XeIF-4AIII and XeIF-4E are distinct: XeIF-4E does not induce epideimal keratin in dissociated cells, (FIG. 2A, lane 2), while XeIF-4AIII does not induce mesoderm in intact animal caps (FIG. 213, lane 1).

Figure 2C:
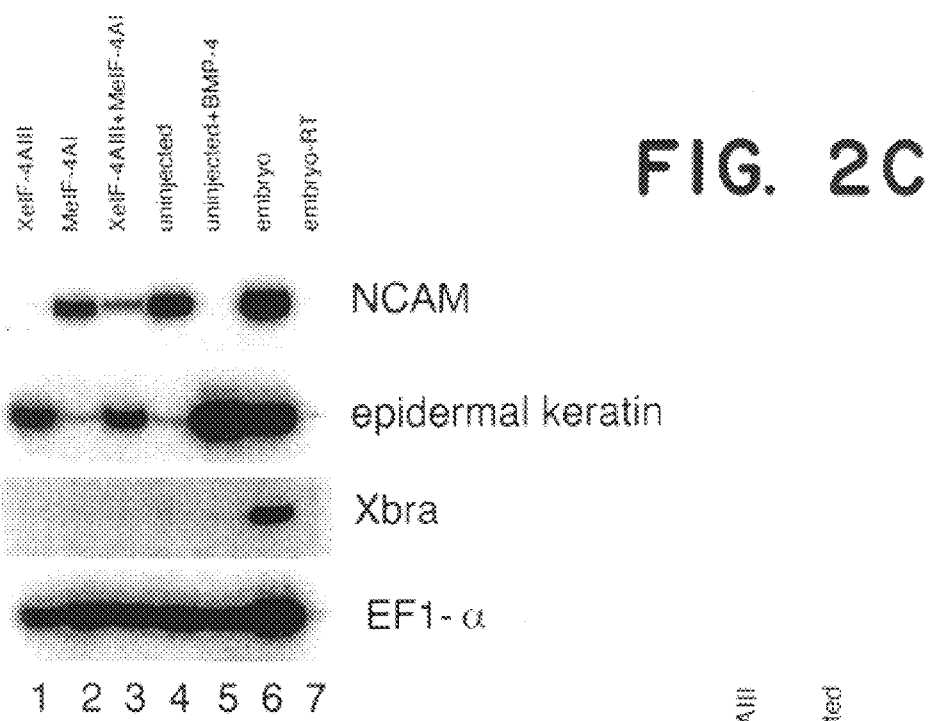

To assess the specificity of XeIF-4AIII, the inductive ability of a related eIF-4A molecule was examined in the dissociated ectoderm assay. Mouse eIF-4AI (MeIF-4AI) [Neilson et al., 1985, supra] did not induce epidermis (FIG. 2C, lane 2), nor did it block induction by XeIF-4AIII when injected at equimolar amounts (FIG. 2C, lane 3). MeIF-4AI and XeIF-4AIII were subcloned into the same expression vector, and both produced a protein band of similar intensity in a rabbit reticulocyte lysate translation systenm The results suggest that eIF-4AI and eIF-4AIII are distinct in their ability to translate mRNAs in the epidennal induction pathway.

Figure 2D:
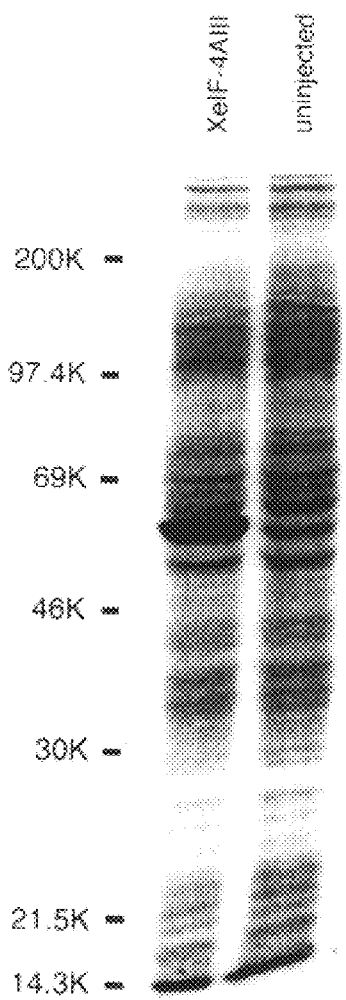

To determine if XeIF-4AIII overexpression results in a general increase in translation rates, oocytes (stage V and VI) were injected with XeIF-4AIII, and then the cells were cultured in the presence of $^{35}$S Methionine (FIG. 2D). Exogenous XeIF-4AIII can be seen as a dark band (of approximately 50 kDa) in the cell fraction from the injected cells. Overexpression of XeIF-4AIII did not lead to an increase in the overall levels of protein synthesis; moreover, no increase was seen in the levels of any specific protein band.

Figure 3A:
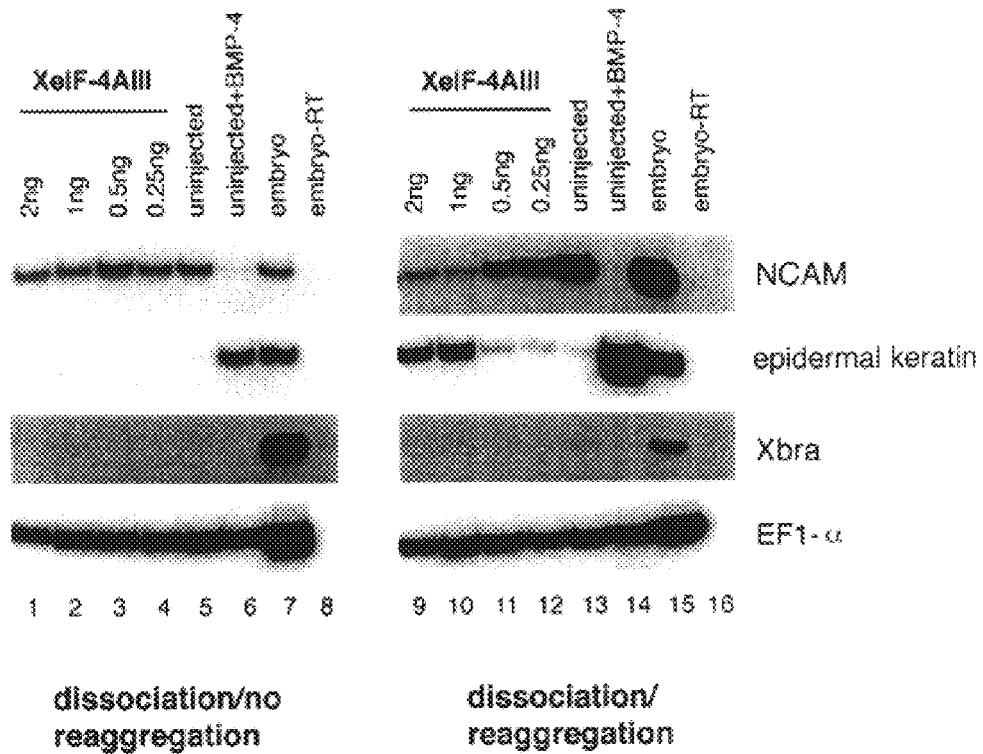
FIGS. 3A–3B show that epidesmal induction by XeIF-4AIII acts through an extracellular intermediate and requires an active BMP signaling pathway.

To address where ectopic XeIF-4AIII acts in the epidermal induction pathway, dissociation experiments were performnded with and without subsequent reaggregation. If ectopic XeIF-4AIII mediates the increased production of an intracellular protein, the resulting epidermal induction should not be dependent on reaggregation. If, on the other hand, XeIF-4AIII overexpression leads to an increase in an extracellular protein, reaggregation might be required to avoid diluting this factor to non-functional levels. In dissociated cultures harvested without r eaggregation, ectopic XeIF-4AIII did not induce epidermis or 4inibit the neural fate (FIG. 3A, lanes 1–8). Neither neuralization nor epidermal induction, per se, requires cell-cell contact: epidermal induction by BMP-4 protein is not dependent on reaggregation (FIG. 3A, compare lanes 6,14), while dissociated cells do not require reaggregation to express neural markers (FIG. 3A, compare lanes 5, 13). These results suggest that XeIF-4AIII overexpression induces epidermis through an extracellular intermediate.

Figure 3B:
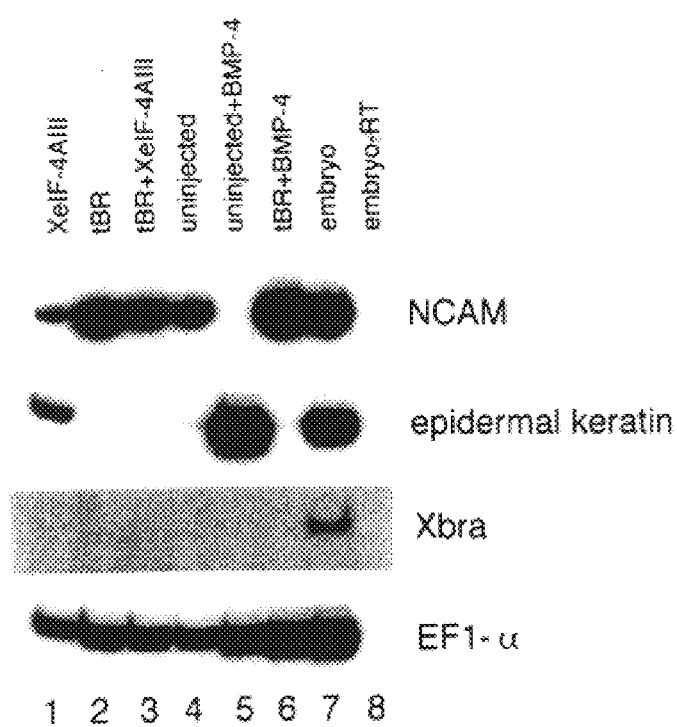

Prior to this study, only BMP-4 has been reported to induce epidermis [Wilson et al., 1995, supra]; thus, it was of interest to see if epidermal induction by XeIF-4AIII is mediated by the BMP signaling pathway. To address this possibility, XeIF-4AIII RNA was co-injected with RNA for a dominant-negative type I BMP receptor (tBR), shown to inhibit signaling of BMP-4 and BMP-2 [Graff et al., *Cell*, 79:169 (1994); Suzuki et al., *Proc. Natl. Acad. Sci. USA*, 91:10255 (1994)]. Overexpression of tBR neuralizes intact caps [Xu et al., *Biochem. Biophys. Res. Commun.*, 212:212 (1995); Sasai et al., *Nature*, 376:333 (1995); Suzuki et al., *Dev. Growth Differ.*, 37:581 (1995)]. Dissociated cells expressing tBR are indistinguishable from uninjected controls (FIG. 3B, compare lanes 2, 4), but are unresponsive to the addition of BMP-4 protein, again expressing only neural, and not epidennal, markers (FIG. 3B, compare lanes 5, 6). Dissociated cells from caps injected with XeIF-4AIII express epidermal keratin (FIG. 3B, lane 1). Dissociated cells that co-express XeIF-4AIII and tBR neuralize (FIG. 3B, lane 3), indicating that XeIF-4AIII requires active signaling through the BMP receptor to induce epidermis in dissociated cells.

eIF-4A has been shown to selectively increase the translation of activin mRNA in a Xenopus oocyte system [Klein and Melton, 1994, supra]. In similar assays, no increase in the translation of BMP-4 mRNA was detected when co-injected with XeIF-4AIII. There are several simple explanations for these results: 1) the BMP-4 construct may lack the complete 5' UTR to which the translation machinery binds in vivo; 2) XeIF-4AIII may act by increasing translation of BMP-2, BMP-7, or other, as yet uncharacterized, epidermal inducers [Note: BMP-4 is an epidermal inducer in dissociated cells. BMP-2 and BMP-7 are also active in the assay]; 3) XeIF-4AIII may increase the production of the soluble inducer indirectly, employing molecular intermediates not present in the oocyte. The present results indicate a positive feedback loop between a soluble epidermal inducer and XeIF-4AIII.

The present results also indicate upon induction by BMP-4 the newly synthesized XeIF-4AIII may differ from preexisting molecules in the type or levels of posttranscriptional modification, or in its association with putative, inhibitory 4A-binding proteins, as have been described for eIF-4E [Sonenberg, 1996, supra]. In maize, eIF-4A phosphorylation occurs during oxygen starvation, and correlates with translational suppression [Webster et al., *J. Biol. Chem.*, 266:23341 (1991)]. The proposed autoregulatory loop offers a means by which XeIF-4AIII could enhance the signal for epidermal induction. Epidermal induction is inhibited in the dorsal ectoderm by direct binding of neuralizing factors in the dorsal ectoderm to BMPs [Weinstein and Heim-nati-Brivanlou, 1997, supra]. In this case, the loop would only be maintained, in the ventral ectoderm, sharpening the boundary between the neurogenic ectodenn and the future epidenmis.

This is the first report of an animal homolog of eIF-4AIII. Two related molecules, eIF-4AI and eIF-4AII, have been reported in mammals [Neilson and Trachsel, 1988, supra]. eIF-4AI and 4AII share high sequence identity, and are incorporated into the eIF-4F complex with similar kinetics [Neilson and Trachsel, 1988, supra]; Yoder-Hil et al., *J. Biol. Chem.*, 268:5566 (1993)1. The results offer the first evidence that a member of the eIF-4A gene family can trigger selective developmental responses. Selective translation by the initiation factor eIF-4E has previously been demonstrated; the specificity of translation in that case is thought to be conferred by the secondary structure of the target mRNA [Sonenberg, 1996, supra; Klein and Melton, 1994, supra]. XeIF-4AIII is clearly divergent from 4AI and 4AII at the sequence level; differences in helicase activity between different eIF-4A family members are one likely form of action, as this would provide an additional level of translational regulation.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

It is further to be understood that all base sizes or almino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated nucleic acid encoding a vertebrate translation initiation factor 4AIII, eIF-4AIII, having an amino acid sequence at least 85% identical to that of SEQ ID NO:2.

2. The isolated nucleic acid of claim 1 wherein the amino acid sequence is SEQ ID NO:2.

3. The isolated nucleic acid of claim 2 wherein the nucleic acid contains the coding sequence of SEQ ID NO:1.

4. The isolated nucleic acid of claim 1 further comprising an heterologous nucleotide sequence.

5. The isolated nucleic acid of claim 4 that encodes a fusion protein or fusion peptide.

6. The isolated nucleic acid of claim 1 operatively linked to an expression control sequence.

7. A unicellular host transfoimed or transfected with the nucleic acid of claim 6.

8. A method of expressing the eIF-4AIII comprising culturing the unicellular host of claim 7 in an appropriate cell culture medium under conditions that provide for expression of the protein by the cell.

9. The method of claim 8 further comprising the step of purifying the eIF-4AIII.

10. An isolated nucleic acid containing 15 or more nucleotides that hybridizes to SEQ ID NO:1 under hybridization conditions comprisinig washes performed in 0.3×SSC/0.1% SDS at 65° C.

11. The isolated nucleic acid of claim 10 that hybridizes to nucleotides 1 to 90 of the coding region of SEQ ID NO:1.

* * * * *